(12) United States Patent
Zhang et al.

(10) Patent No.: US 9,255,106 B2
(45) Date of Patent: Feb. 9, 2016

(54) SUBSTITUTED [1,2,4]TRIAZOLO[4,3-A]PYRAZINES AS PARP-1 INHIBITORS

(71) Applicant: SHANGHAI INSTITUTE OF MATERIA MEDICA, CHINESE ACADEMY OF SCIENCES, Shanghai (CN)

(72) Inventors: Ao Zhang, Shanghai (CN); Zehong Miao, Shanghai (CN); Na Ye, Shanghai (CN); Xiajuan Huan, Shanghai (CN); Zilan Song, Shanghai (CN); Chuanhuizi Chen, Shanghai (CN); Yi Chen, Shanghai (CN); Jian Ding, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 14/418,705

(22) PCT Filed: Jul. 24, 2013

(86) PCT No.: PCT/CN2013/079998
§ 371 (c)(1),
(2) Date: Jan. 30, 2015

(87) PCT Pub. No.: WO2014/019468
PCT Pub. Date: Feb. 6, 2014

(65) Prior Publication Data
US 2015/0166544 A1   Jun. 18, 2015

(30) Foreign Application Priority Data

Aug. 1, 2012   (CN) .......................... 2012 1 0272101

(51) Int. Cl.
| | | |
|---|---|---|
| *A61K 31/4985* | (2006.01) | |
| *C07D 241/38* | (2006.01) | |
| *C07D 487/04* | (2006.01) | |
| *A61K 31/501* | (2006.01) | |
| *A61K 31/502* | (2006.01) | |

(52) U.S. Cl.
CPC .......... *C07D 487/04* (2013.01); *A61K 31/4985* (2013.01); *A61K 31/501* (2013.01); *A61K 31/502* (2013.01)

(58) Field of Classification Search
CPC .......................... A61K 31/4985; C07D 241/38
USPC ........................... 514/249; 544/237, 238, 350
See application file for complete search history.

(56) References Cited

U.S. PATENT DOCUMENTS

2009/0176764 A1   7/2009   Miller et al.

FOREIGN PATENT DOCUMENTS

| CA | 2880739 | * | 2/2014 |
|---|---|---|---|
| CN | 101641014 A | | 2/2010 |
| CN | 101855221 A | | 10/2010 |
| CN | 102898377 A | | 1/2013 |
| CN | 103172619 A | | 6/2013 |
| WO | 2012/019427 A1 | | 2/2012 |
| WO | 2012/072033 A1 | | 7/2012 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, 1, 975-976.*
International Search Report (English Translation) corresponding to PCT/CN2013/079998 mailed Oct. 31, 2013; 5 pages.
Fatima, Sabiha et al., "Molecular docking and 3D-QSAR studies on inhibitors of DNA damage signaling enzyme human PARP-1," *Journal of Receptors and Signal Transduction* (2012); 32(4):214-224.

* cited by examiner

*Primary Examiner* — Douglas M Willis
(74) *Attorney, Agent, or Firm* — Kilpatrick Townsend & Stockton LLP

(57) ABSTRACT

Provided is a piperazinotriazole compound represented by general formula I or a pharmaceutically acceptable salt, stereoisomer, tautomer or hydrate thereof. Also provided are a pharmaceutical composition comprising the compound, a method for preparing the compound and a method of use thereof as a high-selectivity poly(adenosine diphosphate-ribose)polymerase-1 (PARP-1) inhibitor in the preparation of drugs for the prevention and/or treatment of PARP-related diseases.

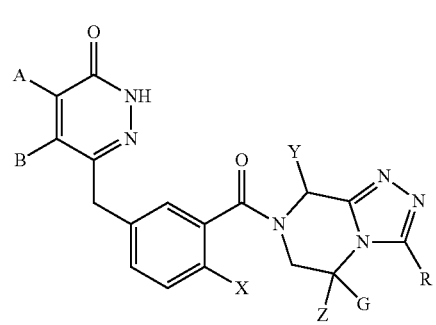

14 Claims, 2 Drawing Sheets

SUBSTITUTED [1,2,4]TRIAZOLO[4,3-A]PYRAZINES AS PARP-1 INHIBITORS

TECHNICAL FIELD

The present invention relates to the field of pharmaceutics, in particular, to piperazinotriazole compounds containing one or more substituents, or the isomers thereof, or the pharmaceutically acceptable salts, esters, prodrugs or hydrates thereof, a pharmaceutical composition containing the same, a preparation method thereof and a use thereof as novel poly (ADP-ribose)polymerase-1 (PARP1) inhibitors with high selectivity in preventing and/or treating PARP related diseases.

BACKGROUND

1. Structural Subtypes and Biological Activities of PARP

Poly(ADP-ribose)polymerases (PARP), which exist in eukaryotic cells and catalyze the polymerization of ADP-ribose, include numerous family members. PARP1 is the earliest-discovered ribozyme in cell that can catalyze ribosylation of poly ADP, and later, other subtypes, such as PARP2, PARP3, PARP4 (VPARP), PARP5a (tankyrase 1), PARP5b (tankyrase 2), PARP7 (TiPARP) and sPARP1, were also separated subsequently. At present, 18 subtypes having potential PARP activity have been determined according to the structure of catalytic domain of PARP1, in which PARP1 has a relatively complete structure. PARP1 contains three main domains, a DNA-binding domain (DBD) at N-terminal, an automodification domain (AMD) and a catalytic domain at C-terminal. The DBD comprises two zinc-finger (ZnF) domains and DNA strand break sensitive element (NLS), and zinc-finger (ZnF) domain will bind to the damaged parts of DNA strand and repair such parts by receiving signals of DNA strand breaks through NLS. In the PARP family, the homology between PARP-2 and PARP1 is the highest which is 69%. Therefore, the currently reported PARP1 inhibitors generally have compatible activity on PARP2 as well.

2. PARP and Diseases

Of the known PARP related functions, PARP1 plays dominantly. These particularly include: 1) repairing DNA and maintaining genome stability; 2) regulating both transcription level and expression of related proteins; 3) affecting replication and differentiation, and maintaining telomere length; 4) regulating cell death and removing damaged cells. Therefore, the DNA repairing mechanism mediated by PARP1 may be inhibited and the damage of radiotherapy and chemotherapy on tumor cell DNA may be increased by inhibiting the PARP1 activity, thereby having a therapeutic effect on tumor.

Although PARP has DNA repair function, but when DNA damage is excessive and difficult to be repaired, PARP will be over-activated and tend to have a "suicide mechanism" leading to over-consumption of the substrate nicotinamide adenine dinucleotide (NAD+) and ATP, depletion of cell energy, and cell necrosis, and ultimately organ tissue injury that is one of the pathogenesis of brain injury and neurodegenerative diseases. It is shown that PARP1 inhibitors exhibit therapeutical effects in animal models of cerebral ischemic injury, shock, Alzheimer and Parkinsonian diseases. Therefore, PARP1 inhibitors have a therapeutic effect for various ischemic and neurodegenerative diseases.

3. PARP Inhibitors

It has been reported by Armin et. al. that the catalytic active sites of PARP1 can be roughly divided into two domains, donor domain and acceptor domain, both using PARP substrate NAD+ as a scaffold. Acceptor domain binds to ADP of poly adenosine ribose diphosphate chains. Donor domain binds to NAD+, and is further divided into three sub-binding domains: nicotinamide-ribose binding site (NI site), phosphate binding site (PH site), and adenosine-ribose binding site (AD site). Most of the reported PARP inhibitors interact with the NI site of PARP and competitively inhibit NAD+, therefore, their structures are similar to that of nicotinamide. For example, AZD2281 (olaparib/KU-59436) developed by AstraZeneca is an oral small molecule PARP inhibitor, has showed promising therapeutical effects in treating ovarian cancer, breast cancer and solid tumor in combination with drugs such as cisplatin, carboplatin, paclitaxel and so on, and is currently in phase II clinical stage.

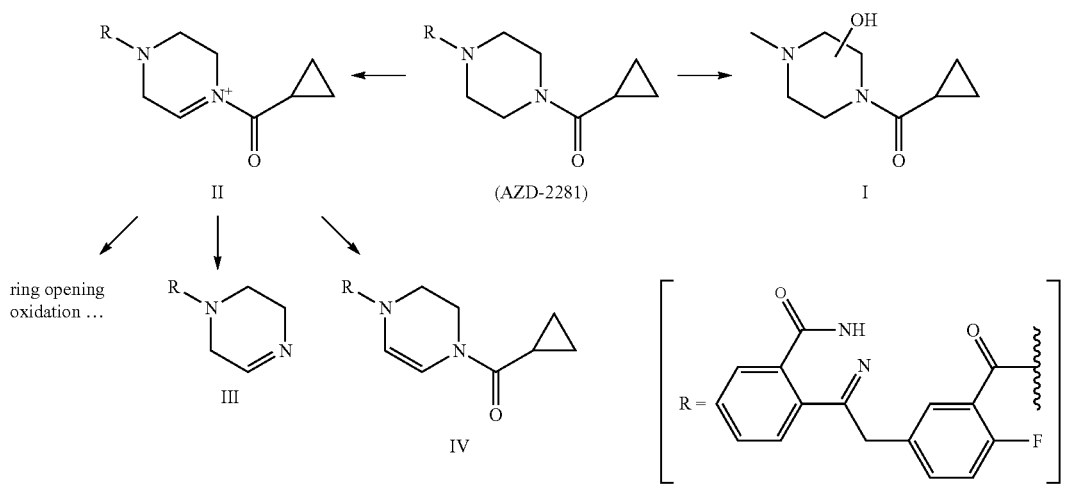

However, the in vivo action time and half-life time (<1 hours) of compound AZD2281 are relatively short, and its bioavailability is low (<15%), which may limit its further development. There are many reasons leading to these shortcomings, and the cyclic tertiary amine of its chemical structure is one of the main reasons that cause the metabolic instability. The cyclic tertiary amine can form oxidation product I or imine intermediate II by oxidase or P450 metabolic enzymes (as shown in the above figure), thus producing a series of oxidative products, including metabolites from N-dealkylation, ring hydroxylation, alpha-carbonylation, N-oxidation, ring opening and so on. All these metabolic products can result in metabolic inactivation of the drug, and even produce toxicity. For example, the cyclic tertiary amine fragment can be metabolized into MPTP (1-methyl-4-phenyl-1,2,3,6-tetrahydrogen pyridine), or phencyclidine (hallucinogenic drugs) and so on through imine intermediate, thereby producing central nervous system toxicity. Meanwhile, AZD2281 has relatively low selectivity within the PARP family, especially to telomerase Tankyrase 1 and Tankyrase 2, which may cause clinical safety concerns.

Therefore, on the basis of a comprehensive analysis on the binding characteristics of the crystal structure of PARP1 with small molecule compounds such as AZD2281, in the present invention, we designed a series of new PARP1 inhibitors by maintaining the key hydrogen bonding sites which will influence activity, i.e. amide segment, and modifying the hydrophobic part, mainly through 1) introducing the piperazinotriazole system with substituents to increase the steric hindrance of tertiary amine, or substituting the metabolic sites to reduce oxidative metabolism ability of compounds under the action of cytochrome P450 enzyme system in vivo, thereby increasing the stability in vivo of molecules and reducing the likelihood of generating toxic metabolites; 2) introducing one or more substituents on the piperazine ring to increase selectivity over telomerase Tankyrase 1 and Tankyrase 2, thereby improving the safety of compounds as PARP1 inhibitors in treating diseases. Therefore, a series of piperazinotriazole compounds containing one or more substituents were developed as novel highly selective PARP1 inhibitors with potential use in treating various ischemic diseases, neurodegenerative disorders and cancers.

SUMMARY OF INVENTION

One object of the present invention is to provide a series of piperazinotriazole compounds containing one or more substituents as shown in formula I, or isomers thereof, or pharmaceutically acceptable salts, esters, prodrugs or hydrates thereof.

Another object of the present invention is to provide a preparation method for the compounds.

Another object of the present invention is to provide a use of the compound as novel highly selective PARP (poly(ADP-ribose)polymerase) inhibitors in the preparation of medicines in preventing and/or treating PARP related diseases. The PARP related diseases include all kinds of ischemic diseases (such as brain, funicle, heart, digestive tract, retina and so on), neurodegenerative diseases (such as Parkinson's disease, Alzheimer's disease, muscular dystrophy and so on) and cancers (such as breast cancer, ovarian cancer, liver cancer, melanoma, prostate cancer, colon cancer, gastric cancer, solid tumor and so on).

Another object of the present invention is to provide a pharmaceutical composition comprising one or more piperazinotriazole compounds or a pharmaceutically acceptable salt, ester, prodrug or hydrate thereof in a therapeutically effective amount.

Another object of the present invention is to provide a method in preventing and/or treating PARP related diseases.

To achieve the above objectives, the present invention provides a series of piperazinotriazole compounds as shown in formula I, or isomers thereof, or pharmaceutically acceptable salts, esters, prodrugs or hydrates thereof,

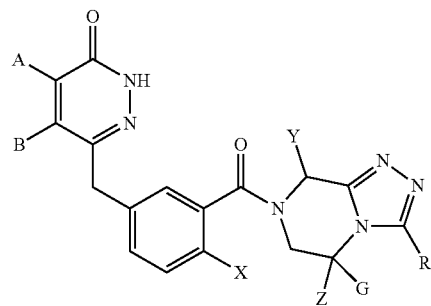

wherein each of A and B independently is a hydrogen or a substituted or unsubstituted C1-C8 hydrocarbonyl, and not both of A and B are hydrogen, in which the substituent for substitution is selected from a group consisting of a halogen, a cyano, a nitro, a hydroxyl and an amino, or, A and B together with the carbon atoms connecting to them form a substituted or unsubstituted C4-C8 aliphatic ring, a substituted or unsubstituted C6-C10 aromatic ring, a substituted or unsubstituted 4-8 membered heterocyclic ring containing one to three atoms selected from N, O or S, or a substituted or unsubstituted 5-8 membered heteroaromatic ring containing one to three atoms selected from N, O or S, in which the substituent for substitution is selected from a group consisting of a halogen, a cyano, a nitro, a hydroxyl and an amino, X is a hydrogen, a halogen, a hydroxyl or a cyano, Y is a hydrogen or a substituted or unsubstituted C1-C8 alkyl, in which the substituent for substitution is selected from a group consisting of a halogen, a cyano, a nitro, a hydroxyl, an amino, a C1-C6 alkoxy, a C2-C6 alkyl carbonyl, a C2-C6 alkoxy carbonyl, a C2-C6 alkenyl, a C2-C6 alkynyl and a C6-C10 aryl, G is a hydrogen, a C1-C6 alkyl, a C1-C6 alkoxy, a C2-C6 alkyl carbonyl, or a C1-C6 alkyl amino or a (C1-C6 alkyl)$_2$ amino, Z is a hydrogen, a C1-C6 alkyl, a C1-C6 alkoxy, a C2-C6 alkyl carbonyl, or a C1-C6 alkyl amino or a (C1-C6 alkyl)$_2$ amino, and not all of Y, G and Z are hydrogen, R is selected from a hydrogen or a substituted or unsubstituted C1-C8 alkyl, in which the substitutent for substitution is selected from a group consisting of a halogen, a cyano, a nitro, a hydroxyl, an amino, a C1-C6 alkoxy, a C2-C6 alkyl carbonyl, a C2-C6 alkoxy carbonyl and a C6-C10 aryl, preferably, in the compound of formula I, each of A and B is independently a hydrogen, a substituted or unsubstituted C1-C8 alkyl, a substituted or unsubstituted C2-C8 alkenyl, or a substituted or unsubstituted C2-C8 alkynyl, and not both of A and B are hydrogen, in which the substituent for substitution is selected from a group consisting of a halogen, a cyano, a nitro, a hydroxyl and an amino, or, A and B together with carbon atoms connecting to them form a substituted or unsubstituted C4-C7 aliphatic ring, a substituted or unsubstituted C6-C8 aromatic ring, a substituted or unsubstituted 4-7 membered heterocyclic ring containing one to three atoms selected from N, O or S, or a substituted or unsubstituted 5-7 membered heteroaromatic ring containing one to three atoms selected from N, O or S, in which the substituent for substitution is selected from a group consisting of a halogen, a cyano, a nitro, a hydroxyl and an amino, X is a hydrogen, a halogen, a hydroxyl or a cyano;

Y is a hydrogen or a substituted or unsubstituted C1-C6 alkyl, and the substituent for substitution is selected from a group consisting of a halogen, a cyano, a nitro, a hydroxyl, an amino, a C1-C4 alkoxy, a C2-C4 alkyl carbonyl, a C2-C4 alkoxy carbonyl, a C2-C4 alkenyl, a C2-C4 alkynyl and a C6-C8 aryl, G is a hydrogen, a C1-C4 alkyl, a C1-C4 alkoxy, a C2-C4 alkyl carbonyl, a C1-C4 alkyl amino or a (C1-C4 alkyl)$_2$ amino, Z is a hydrogen, a C1-C4 alkyl, a C1-C4 alkoxy, a C2-C4 alkyl carbonyl, a C1-C4 alkyl amino or a (C1-C4 alkyl)$_2$ amino, and not all of Y, G and Z are hydrogen;

R is selected from a hydrogen, a substituted or unsubstituted C1-C6 alkyl, and the substituent for substitution is selected from a group consisting of a halogen, a cyano, a nitro, a hydroxyl, an amino, a C1-C4 alkoxy, a C2-C4 alkyl carbonyl, a C2-C4 alkoxy carbonyl and a C6-C8 aryl;

more preferably, in the compound of formula I, each of A and B is independently a hydrogen, a substituted or unsubstituted C1-C6 alkyl, and not both of A and B are hydrogen, in which the substituent for substitution is selected from a group consisting of a halogen, a cyano, a nitro, a hydroxyl and an amino, or, A and B together with carbon atoms connecting to them form a substituted or unsubstituted C4-C7 aliphatic ring, a substituted or unsubstituted C6-C8 aromatic ring, in which the substituent for substitution is selected from a group consisting of a halogen, a cyano, a nitro, a hydroxyl and an amino, X is a hydrogen, a halogen, a hydroxyl or a cyano;

Y is a hydrogen or a substituted or unsubstituted C1-C6 alkyl, and the substituent for substitution is selected from a group consisting of a halogen, a cyano, a nitro, a hydroxyl, an amino, a C1-C4 alkoxy, a C2-C4 alkyl carbonyl, a C2-C4 alkoxy carbonyl, a C2-C4 alkenyl, a C2-C4 alkynyl and a C6-C8 aryl, G is a hydrogen, a C1-C4 alkyl, a C1-C4 alkoxy, a C2-C4 alkyl carbonyl, a C1-C4 alkyl amino or a (C1-C4 alkyl)$_2$ amino, Z is a hydrogen, a C1-C4 alkyl, a C1-C4 alkoxy, a C2-C4 alkyl carbonyl, a C1-C4 alkyl amino or a (C1-C4 alkyl)$_2$ amino, and not all of Y, G and Z are hydrogen;

R is selected from a hydrogen, a substituted or unsubstituted C1-C6 alkyl, and the substituent for substitution is selected from a group consisting of a halogen, a cyano, a nitro, a hydroxyl, and a amino;

more preferably, in the compound of formula I, each of A and B is independently a hydrogen, C1-C4 alkyl, and not both of A and B are hydrogen, or, A and B together with carbon atoms connecting to them form a substituted or unsubstituted C4-C6 aliphatic ring, a substituted or unsubstituted C6-C8 aromatic ring, in which the substituent for substitution is selected from a group consisting of a halogen, a cyano, a nitro, a hydroxyl and a amino, X is a hydrogen, a halogen, a hydroxyl or a cyano;

Y is a hydrogen or a substituted or unsubstituted C1-C4 alkyl, and the substituent for substitution is selected from a group consisting of a halogen, a cyano, a nitro, a hydroxyl, an amino, a C1-C4 alkoxy, a C2-C4 alkoxy carbonyl, a C2-C4 alkenyl, and a phenyl, G is a hydrogen, a C1-C4 alkyl, a C1-C4 alkoxy, a C1-C4 alkyl amino or a (C1-C4 alkyl)$_2$ amino, Z is a hydrogen, a C1-C4 alkyl, a C1-C4 alkoxy, a C1-C4 alkyl amino or a (C1-C4 alkyl)$_2$ amino, and not all of Y, G and Z are hydrogen;

R is selected from a hydrogen, or a substituted or unsubstituted C1-C4 alkyl, and the substituent for substitution is selected from a group consisting of a halogen, a cyano, a nitro, a hydroxyl, and an amino;

more preferably, in the compound of formula I, each of A and B is independently a hydrogen or a methyl, and not both of A and B are hydrogen, or, A and B together with carbon atoms connecting to them form a phenyl, X is a hydrogen or a halogen;

Y is a hydrogen, a methyl, a 2,2,2-trifluoroethyl, an allyl, an ethoxy carbonyl ethyl or a benzyl, G is a hydrogen, a methyl, an ethyl, a methoxyl, or a dimethyl amino, Z is a hydrogen, a methyl, an ethyl, a methoxyl, or a dimethyl amino, and not all of Y, G and Z are hydrogen;

R is a hydrogen, a fluoromethyl, a difluoromethyl, or a trifluoromethyl.

The ordinary skilled in the art should understand that piperazinotriazole compounds as shown in formula I can exist in an isomer form. The isomer of piperazinotriazole compounds as shown in formula I may include, but not limited to, the structure as shown in formula II, The typical compounds of the present invention include, but not limited to, the following compounds,

| Compound | Structure |
|---|---|
| S1 | 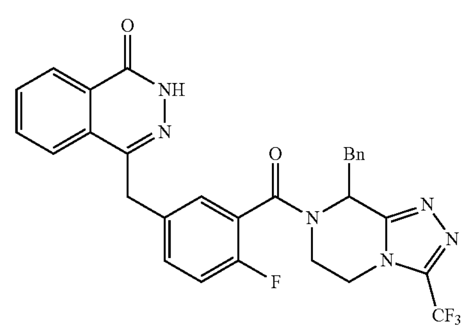 [SMILES: O=C(c1cc(Cc2n[nH]c(=O)c3ccccc23)ccc1F)N1CCn2c(nnc2C(F)(F)F)C1Cc1ccccc1] |

| Compound | Structure |
|---|---|
| S2 | 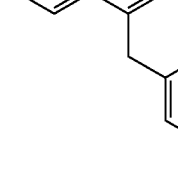 |
| S3 | 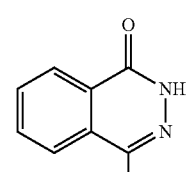 |
| S4 | 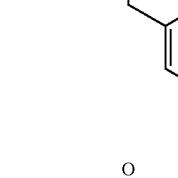 |
| S5 | 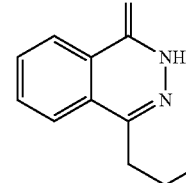 |
| S6 | 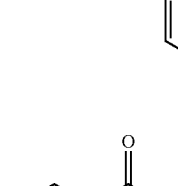 |
| S7 | 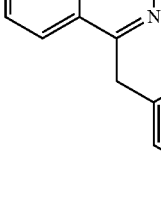 |
| S8 | 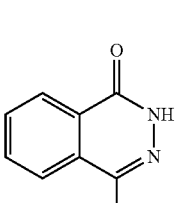 |
| S9 |  |
| S10 | 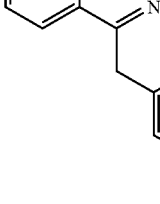 |

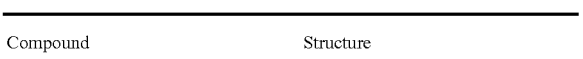
| Compound | Structure |
|---|---|
| S11 | 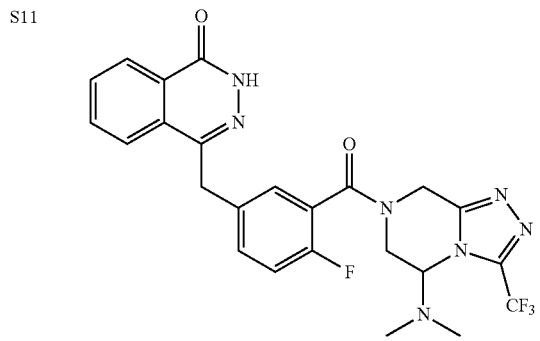 |
| S12 | 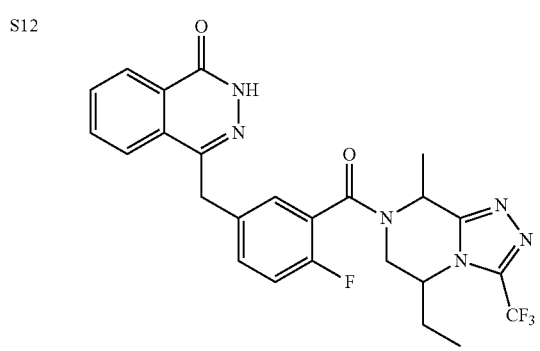 |
| S13 | 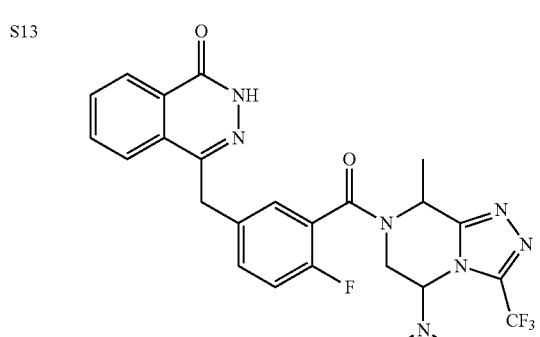 |
| S14 | 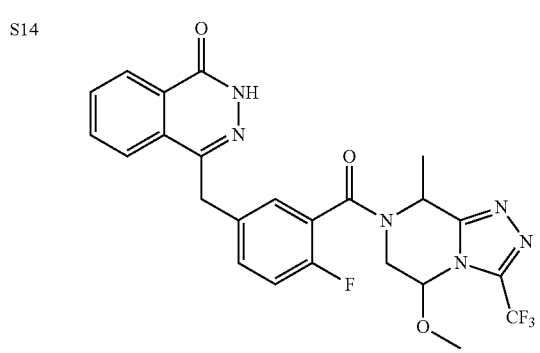 |
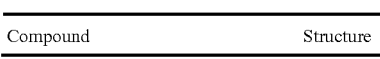
| Compound | Structure |
|---|---|
| S15 | 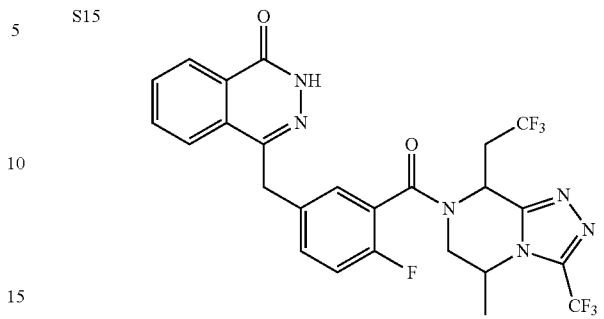 |
| S16 | 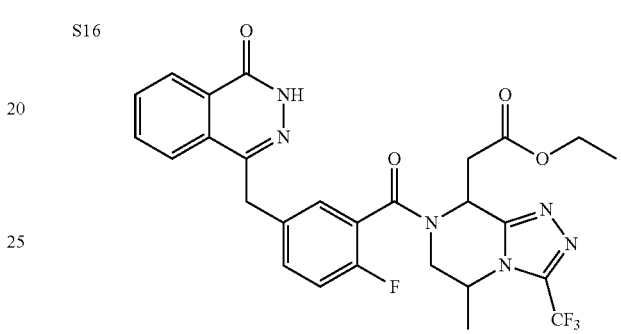 |
| S17 | 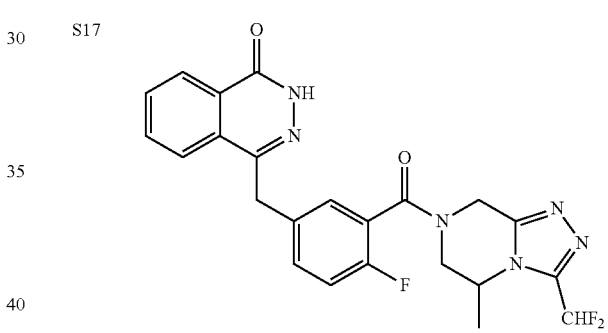 |
| S18 | 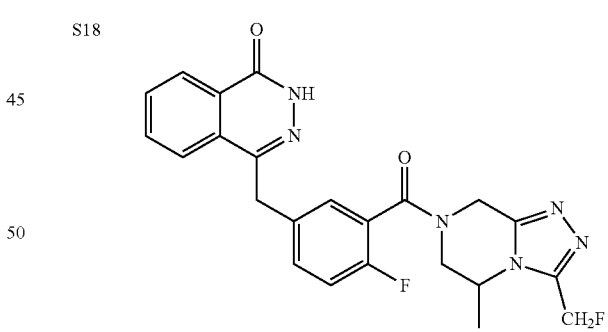 |
| S19 | 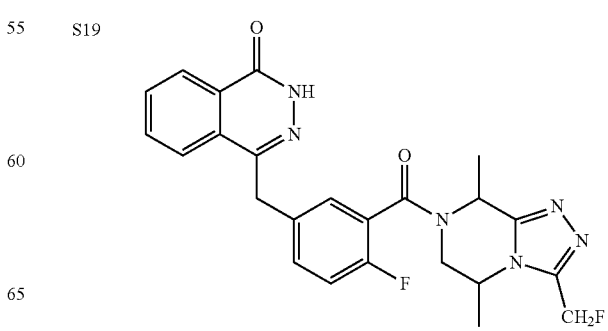 |

| Compound | Structure |
|---|---|
| S20 | 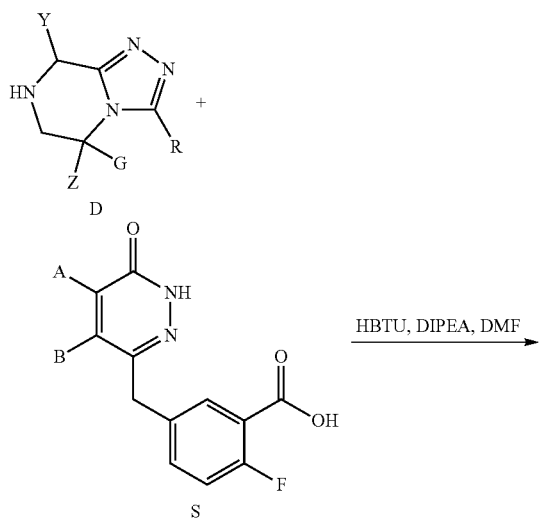 |
| S21 | 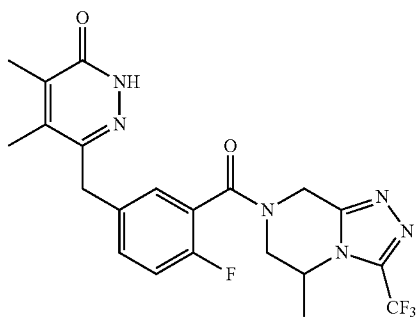 [SMILES: Cc1c(Cc2ccc(F)c(C(=O)N3Cc4nnc(C(F)(F)F)n4C(C)C3)c2)n[nH]c(=O)c1C] |
| S22 | 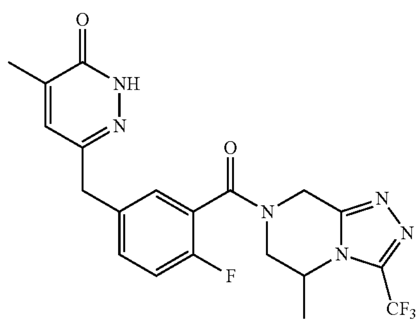 [SMILES: Cc1cc(Cc2ccc(F)c(C(=O)N3Cc4nnc(C(F)(F)F)n4C(C)C3)c2)n[nH]c1=O] |

Another aspect of the present invention provides a method for preparing piperazinotriazole compounds as shown in formula I, comprising the following steps,

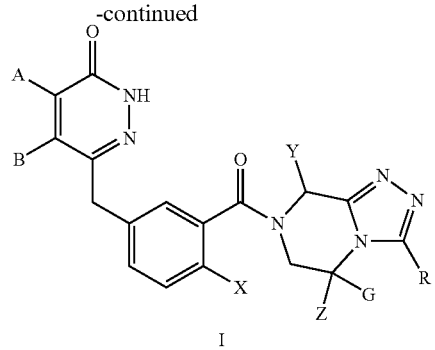

Raw material S can be synthesized according to J. Med. Chem. 2008, 51, 6581-6591; US2008161280, and WO2007138351, wherein HBTU is O-benzotriazole-N,N,N', N'-tetramethyl uranium hexafluorophosphate, DIPEA is diisopropyl ethylamine, and DMF is N,N-dimethyl formamide.

The raw materials S (1 eq) and amine D (1 eq) which are commercially purchased or synthesized are dissolved in DMF, and then HBTU and DIPEA are sequentially added in an ice bath. The resultant mixture is gradually warmed up to room temperature and stirred overnight. Water is added into the mixture in an ice bath, and the resulting mixture is extracted with dichloromethane. The dichloromethane layer is washed with saturated aqueous sodium chloride, dried, and evaporated to remove solvent. The residue is separated by column chromatography to obtain piperazinotriazole compounds as shown in formula I.

Another aspect of the invention further provides a use of piperazinotriazole compounds as shown in formula I, or an isomer thereof, or a pharmaceutically acceptable salt, ester, prodrug or hydrate thereof, as a novel highly selective PARP1 inhibitor in the preparation of a drug for preventing and/or treating PARP (poly adenosine two phosphate ribose polymerase) related diseases, i.e. all kinds of ischemic diseases (such as brain, funicle, heart, digestive tract, retina and so on), neurodegenerative diseases (such as Parkinson's disease, Alzheimer's disease, muscular dystrophy and so on) and cancers (such as breast cancer, ovarian cancer, liver cancer, melanoma, prostate cancer, colon cancer, gastric cancer, other solid tumors and so on).

Another aspect of the invention provides a pharmaceutical composition, comprising one or more piperazinotriazole compounds of general formula I or a pharmaceutically acceptable salt, ester, prodrug or hydrate thereof in a therapeutically effective amount, and optionally further comprising a pharmaceutically acceptable carrier or excipient.

Another aspect of the invention provides a PARP1 inhibitor, comprising one or more piperazinotriazole compounds of general formula I or a pharmaceutically acceptable salt, ester, prodrug or hydrate thereof in a therapeutically effective amount, and optionally further comprising a pharmaceutically acceptable carrier or excipient.

Another aspect of the invention provides a method for preventing and/or treating PARP related diseases, comprising a procedure of administering piperazinotriazole compounds of general formula I or a pharmaceutically acceptable salt, ester, prodrug or hydrate thereof, or the above pharmaceutically composition of the present invention in a therapeutically effective amount to a patient.

DETAILED DESCRIPTION OF INVENTION

Figure 1:
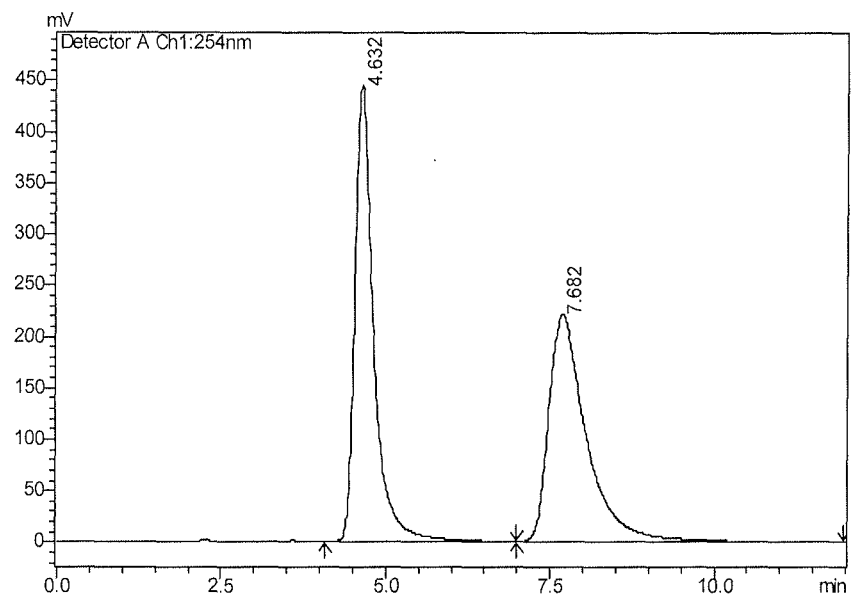
FIG. 1 is a spectrum of racemate S3.

The present invention will be further illustrated below with reference to specific examples, which should not be used to limit the scope of the invention.

1. Preparation Example $^1$H-NMR is determined by Varian MercuryAMX300 instrument. MS is determined by VG ZAB-HS or VG-7070 instrument, using EI source (70 ev) unless indicated otherwise. All solvents are distilled before use. Anhydrous solvent used are obtained according to the standard drying methods. Unless indicated otherwise, all reactions are conducted under the protection of nitrogen and monitored by TLC, and during post processing, all reactions are washed by saturated sodium chloride solution and dried by anhydrous sodium sulfate. Unless indicated otherwise, product is purified using column chromatography on silica gel (200~300 mesh); the silica gel (200~300 mesh) is produced by Qingdao Haiyang Chemical Co., Ltd, GF254 thin layer silica gel plate is produced by Yantai Jiangyou Silica Gel Development Co., Ltd.

1. Synthesis of Compound S1

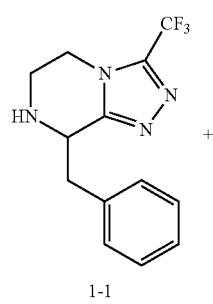

1-1

+

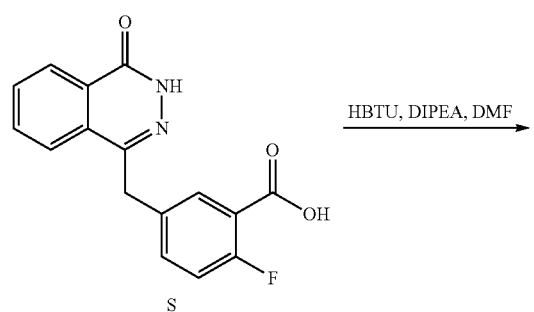

HBTU, DIPEA, DMF →

-continued

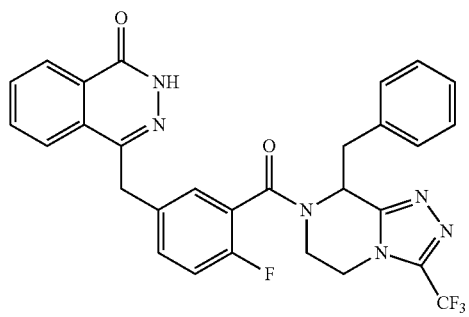

S1 wherein, raw material S was synthesized according to the procedures in J. Med. Chem. 2008, 51, 6581-6591, raw material 1-1 was synthesized according to the procedures in J. Med. Chem. 2008, 51, 589-602, HBTU is O-benzotriazole-N,N,N',N'-tetramethyluronium hexafluorophosphate, DIPEA is diisopropylethylamine, and DMF is N,N-dimethylformamide.

Intermediate S (1 eq) and 8-benzyl-3-trifluoromethyl-5,6,7,8-tetrahydro[1,2,4]triazolo[4,3-a]piperazine (1 eq) were dissolved in DMF, and then HBTU (1.2 eq), DIPEA (2 eq) were added successively in an ice bath. The mixture was warmed gradually to room temperature and stirred overnight. Water was added in an ice bath, and the mixture was extracted twice with dichloromethane. The dichloromethane layer was washed with saturated sodium chloride solution, dried and evaporated to remove the solvent. The residue was purified by column chromatography to provide S1 as white foam. $^1$H NMR (300 MHz, CDCl$_3$) δ 11.69 (s, 0.5H), 11.45 (s, 0.5H), 8.44 (s, 1H), 7.97-7.62 (m, 3H), 7.41-6.69 (m, 7H), 6.33 (s, 1H), 5.26 (d, J=40.2 Hz, 1H), 4.29 (s, 2H), 4.09 (s, 1.5H), 3.89 (s, 1H), 3.62 (m, 1.5H), 3.18 (s, 1H), 2.86 (m, 1H).

2. Synthesis of Compound S2

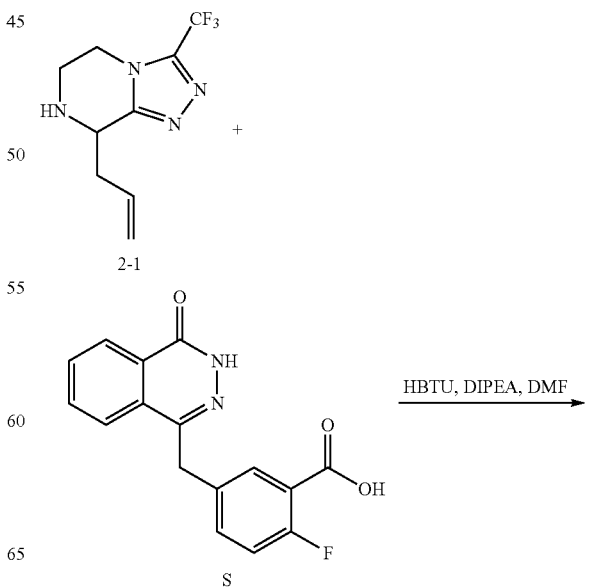

2-1

+

S

HBTU, DIPEA, DMF →

-continued

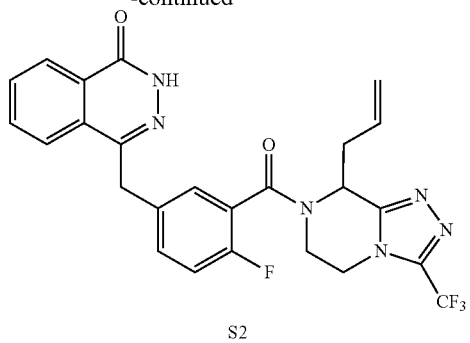

S2 wherein, raw material 2-1 was synthesized according to the procedures in J. Med. Chem. 2008, 51, 589-602.

The synthetic method for S2 is identical to that for S1. The analytical data of S2 are listed as follows: $^1$H NMR (300 MHz, CDCl$_3$) δ 11.59 (s, 0.65H), 11.47 (s, 0.35H), 8.56-8.29 (m, 1H), 7.90-7.59 (m, 3H), 7.33 (m, 2H), 7.06 (m, 1H), 6.21-6.17 (m, 0.5H), 5.86 (m, 0.5H), 5.47-4.72 (m, 3H), 4.30 (s, 2H), 4.21-3.82 (m, 2H), 3.71 (m, 1H), 3.47-2.47 (m, 3H).

3. Synthesis of Compound S3

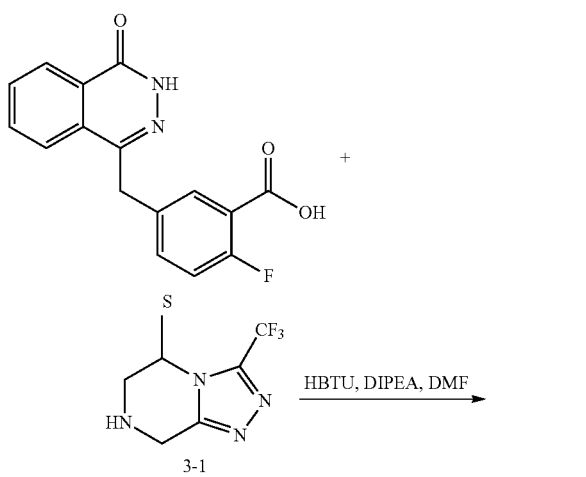

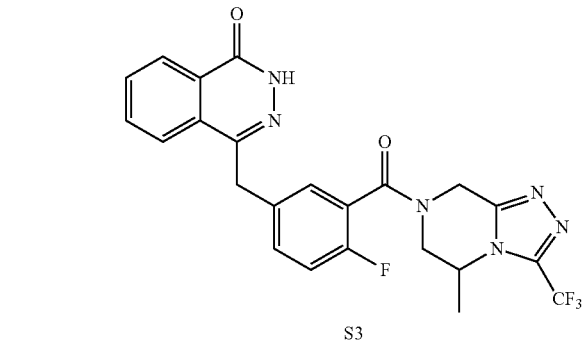

S3 wherein, raw material 3-1 was synthesized according to J. Med. Chem. 2008, 51, 589-602.

The synthetic method for S3 is identical to that for S1. The analytical data of S3 are listed as follows: $^1$H NMR (300 MHz, CDCl$_3$) δ 12.19 (s, 0.33H), 12.01 (s, 0.67H), 8.37 (d, J=7.4 Hz, 1H), 7.71 (m, 3H), 7.48-7.28 (m, 2H), 7.04 (t, J=8.8 Hz, 1H), 4.88 (m, 1H), 4.76-4.41 (m, 2H), 4.22 (s, 2H), 3.72 (s, 1H), 3.46-3.41 (m, 1H), 1.49 (d, J=6.3 Hz, 3H).

4. Synthesis of Compound S4

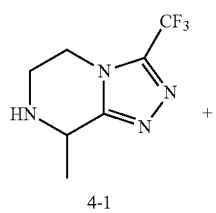

4-1

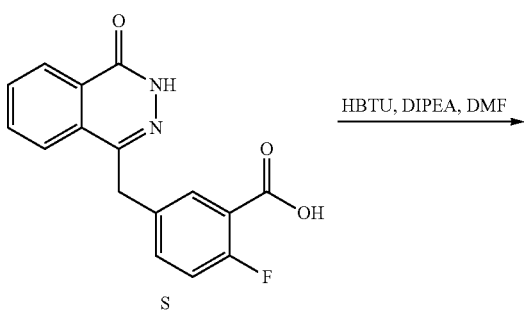

S4 wherein, raw material 4-1 was synthesized according to J. Med. Chem. 2008, 51, 589-602.

The synthetic method for S4 is identical to that for S1. The analytical data of S4 are listed as follows: $^1$H NMR (300 MHz, CDCl$_3$) δ 12.13 (s, 1H), 8.33 (d, J=6.9 Hz, 1H), 7.65 (m, 3H), 7.35 (s, 2H), 7.01 (t, J=8.1 Hz, 1H), 6.02 (s, 0.5H), 5.18-4.88 (m, 0.5H), 4.25 (s, 2H), 4.20-3.80 (m, 3H), 3.68 (m, 1H), 1.63 (d, J=4.5 Hz, 2H), 1.46 (s, 1H).

5. Synthesis of Compound S5

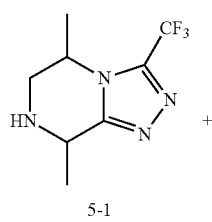

5-1

-continued

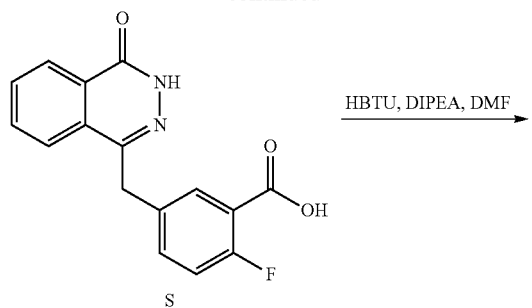

HBTU, DIPEA, DMF →

-continued

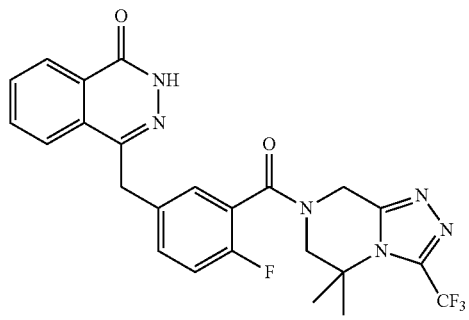

S6 wherein, raw material 6-1 was synthesized according to J. Med. Chem. 2008, 51, 589-602.

The synthetic method for S6 is identical to that for S1. The analytical data of S6 are listed as follows: $^1$H NMR (300 MHz, CDCl$_3$) δ 12.11 (s, 0.3H), δ 11.94 (s, 0.7H), 8.39 (d, J=7.2 Hz, 1H), 7.70 (d, J=7.2 Hz, 3H), 7.36 (d, J=5.4 Hz, 2H), 7.03 (t, J=8.7 Hz, 1H), 5.14 (s, 0.5H), 4.76 (s, 1.5H), 4.27 (s, 2H), 3.98 (s, 1.5H), 3.52 (s, 0.5H), 1.62 (s, 4.35H), 1.40 (s, 1.68H).

7. Synthesis of Compound S7

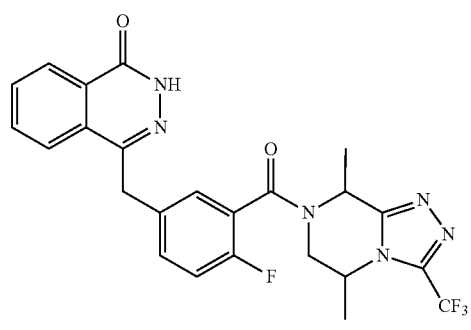

S5 wherein, raw material 5-1 was synthesized according to J. Med. Chem. 2008, 51, 589-602.

The synthetic method for S5 is identical to that for S1. The analytical data of S5 are listed as follows: $^1$H NMR (300 MHz, CDCl$_3$) δ 11.93 (s, 0.3H), 11.79 (d, J=13.8 Hz, 0.7H), 8.43 (d, J=7.5 Hz, 1H), 7.73 (m, 3H), 7.36 (m, 2H), 7.07 (m, 1H), 6.10 (t, J=6.9 Hz, 0.25H), 5.09 (d, J=7.2 Hz, 0.25H), 4.89 (d, J=14.1 Hz, 0.25H), 4.67 (s, 0.25H), 4.55-4.37 (m, 1H), 4.35-4.24 (m, 2H), 3.87-3.53 (m, 0.5H), 3.46-3.18 (m, 1H), 3.12-3.05 (m, 0.5H), 1.71-1.43 (m, 6H).

6. Synthesis of Compound S6

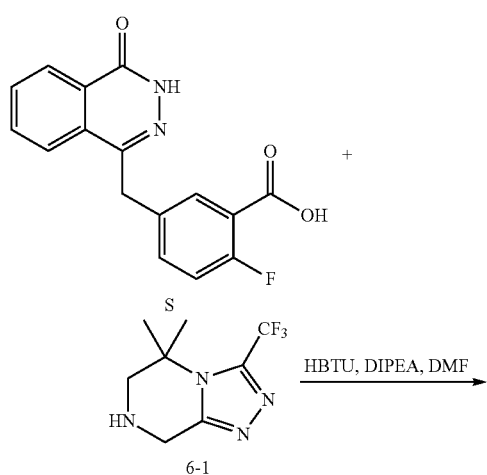

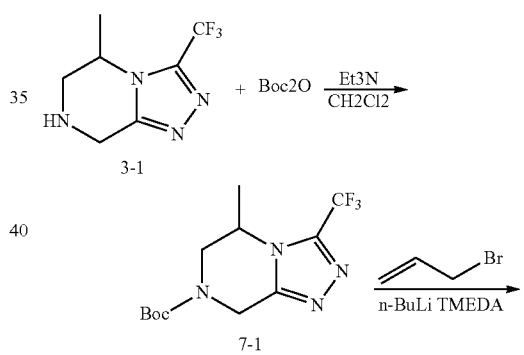

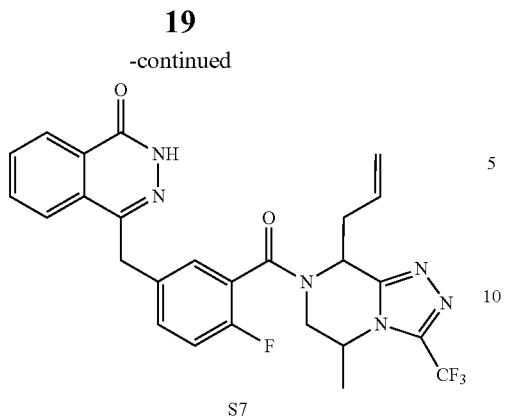

S7 wherein, raw material 7-1 was synthesized according to J. Med. Chem. 2008, 51, 589-602, and TMEDA is tetramethylethylenediamine.

Synthesis of Intermediate 7-2

Raw material 7-1 (1 eq) was dissolved in tetrahydrofuran, TMEDA (1.5 eq) was added at −78° C. After 10 mins, n-BuLi was slowly added dropwise. After another 10 mins, allyl bromide was added. Upon addition, refrigeration was stopped after 20 mins. The reaction was quenched with saturated ammonium chloride, and extracted twice with dichloromethane. The dichloromethane layer was washed with saturated sodium chloride solution, dried and evaporated to remove the solvent. The residue was purified by column chromatography to provide intermediate 7-2. $^1$H NMR (300 MHz, CDCl$_3$) δ 5.98-5.36 (m, 2H), 5.24-4.83 (m, 2H), 4.63-4.26 (m, 2H), 3.29 (m, 1H), 2.82 (s, 1H), 2.67 (m, H), 1.55-1.37 (m, 12H).

Synthesis of Intermediate 7-3

Raw material 7-2 was dissolved in ethanol, and 6 N hydrochloric acid was added. The mixture was stirred at room temperature overnight, and directly evaporated to remove the solvent under reduced pressure for further use.

The synthetic method for S7 is identical to that for S1. The analytical data of S7 are listed as follows: $^1$H NMR (300 MHz, CDCl$_3$) δ 11.89-11.78 (m, 1H), 8.42 (d, J=7.5 Hz, 1H), 7.72 (m, 3H), 7.38 (m, 2H), 7.06 (m, 1H), 6.25-6.19 (m, 0.5H), 5.87 (m, 0.5H), 5.49-4.73 (m, 3H), 4.30 (s, 2H), 4.20-3.80 (m, 3H), 3.45-2.44 (m, 2H), 1.72-1.45 (m, 3H).

8. Synthesis of Compound S8

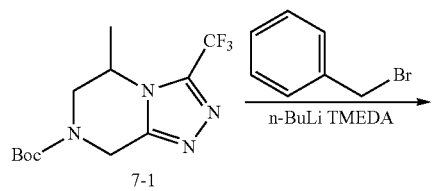

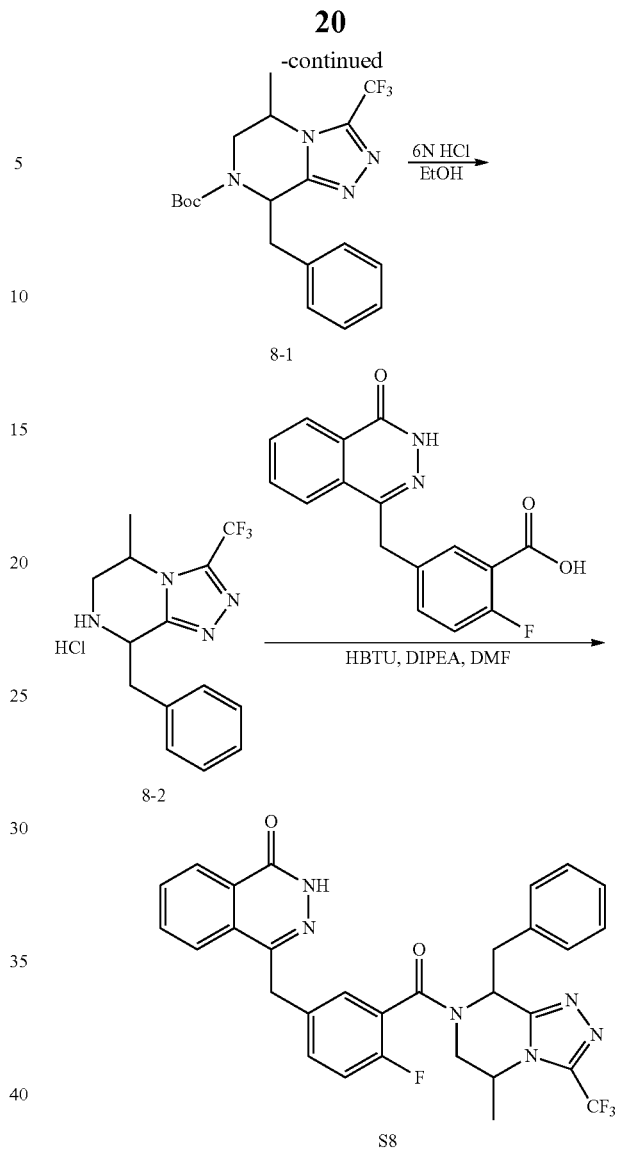

Synthesis of Intermediate 8-1

The synthetic method is identical to that for 7-2. The analytical data of 8-1 are listed as follows: $^1$H NMR (300 MHz, CDCl$_3$) δ 7.38-7.19 (m, 3H), 7.12 (d, J=6.0 Hz, 2H), 5.68 (dd, J=9.1, 3.8 Hz, 1H), 4.49-4.15 (m, 2H), 3.39 (d, J=11.4 Hz, 1H), 3.19 (dd, J=13.7, 9.7 Hz, 1H), 2.91 (dd, J=14.3, 10.1 Hz, 1H), 1.30-1.07 (m, 12H).

Synthesis of Intermediate 8-2

Raw material 8-1 was dissolved in ethanol, and 6 N hydrochloric acid was added. The mixture was stirred at room temperature overnight and directly evaporated to remove the solvent under reduced pressure for further use.

Synthesis of the Final Product S8

The synthetic method for S8 is identical to that for S1. The analytical data of S8 are listed as follows: $^1$H NMR (300 MHz, CDCl$_3$) δ 11.70 (s, 0.5H), 11.46 (s, 0.5H), 8.44 (s, 1H), 7.78 (m, 3H), 7.43-6.68 (m, 7H), 6.35 (s, 1H), 5.28 (m, 1H), 5.17-4.67 (m, 1H), 4.30 (s, 2H), 4.09 (m, 2H), 3.48-3.14 (m, 2H), 1.75-1.48 (m, 3H).

9. Synthesis of Compound S9

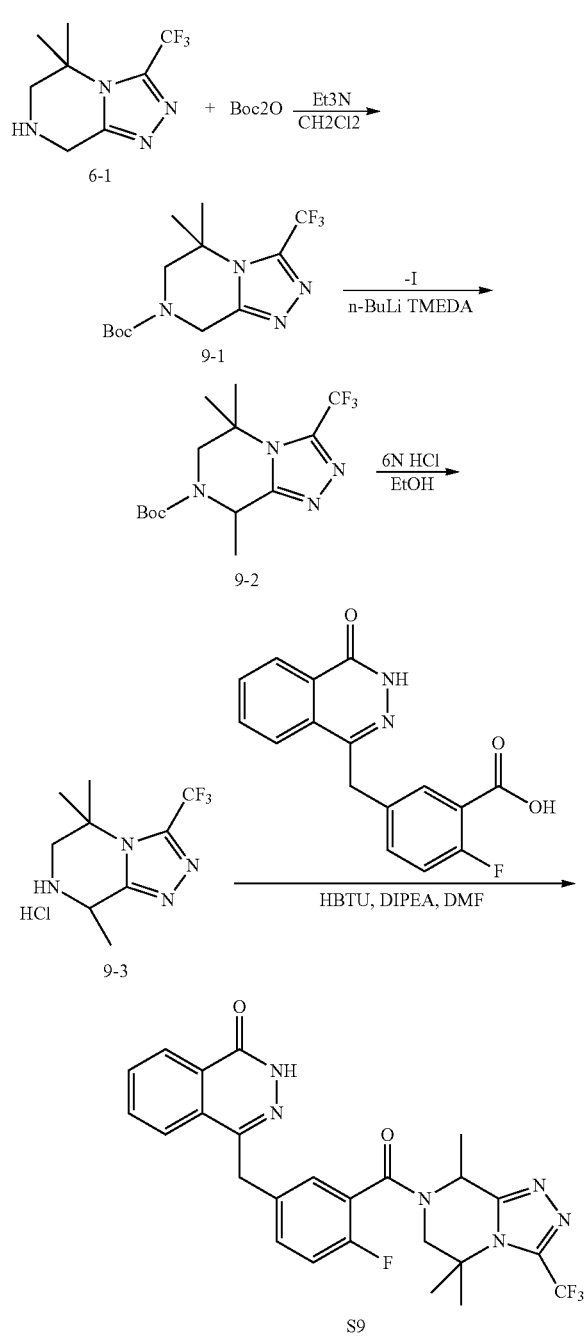

9-3

S9

The synthetic methods for S9 and its intermediates are identical to those for S8.

The analytical data of S9 are listed as follows: ¹H NMR (300 MHz, CDCl₃) δ 12.12 (s, 0.4H), δ 11.96 (s, 0.6H), 8.36 (d, J=7.2 Hz, 1H), 7.70 (d, J=7.2 Hz, 3H), 7.36 (d, J=5.4 Hz, 2H), 7.03 (t, J=8.7 Hz, 1H), 6.00 (s, 0.5H), 5.15-4.85 (m, 0.5H), 4.28 (s, 2H), 3.95 (s, 1.5H), 3.50 (s, 0.5H), 1.6-01.34 (m, 9H).

10. Synthesis of Compound S10

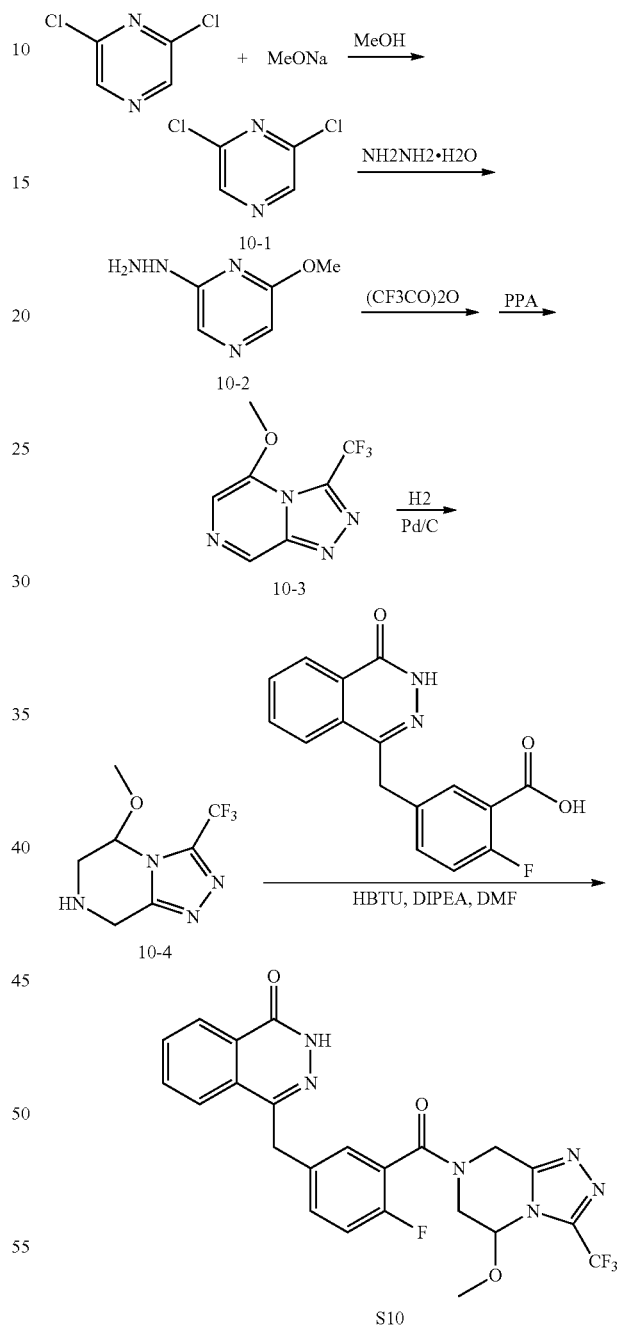

S10 wherein, raw material 10-1 was synthesized according to the procedures in *Journal of Heterocyclic Chemistry*, 2005, 42(4), 691-694.

Synthesis of Intermediate 10-2

Raw material 10-1 was dissolved in 80% hydrazine hydrate, and the mixture was heated to 120° C. After the reaction was completed, the mixture was cooled to room temperature and then placed in a refrigerator. A great amount of solids was precipitated, filtered and dried to give a crude product 10-2. ¹H NMR (300 MHz, DMSO) δ 7.48 (s, 1H), 7.41 (s, 1H), 7.35 (s, 1H), 4.11 (s, 2H), 3.99 (s, 3H).

Synthesis of Intermediate 10-3

Trifluoroacetic anhydride was cooled in an ice bath, and then intermediate 10-2 was added in portions. The mixture was stirred at this temperature for 10 mins, and then warmed slowly to room temperature. After the reaction was completed, the reaction mixture was evaporated under reduced pressure and then polyphosphoric acid was added. The mixture was heated to 120° C. and stirred overnight. The reaction mixture was cooled, and then poured into cooled concentrated aqueous ammonia. The resulting mixture was filtered to give a crude product 10-3. ¹H NMR (300 MHz, DMSO) δ 9.51 (s, 1H), 8.08 (s, 1H), 4.02 (s, 3H).

Synthesis of Intermediate 10-4

Intermediate 10-3 was dissolved in methanol, and palladium on carbon was added. The mixture was reacted under hydrogen atmosphere overnight. After the reaction completed, the palladium on carbon residue was filtered off, and the filtrate was concentrated to give intermediate 10-4. ¹H NMR (300 MHz, CDCl₃) δ 5.43 (t, J=7.5 Hz, 1H), 4.28 (d, J=16.8 Hz, 1H), 4.07 (d, J=16.8 Hz, 1H), 3.39 (s, 3H), 3.18 (dd, J=13.5, 3.9 Hz, 1H), 3.03 (d, J=13.5 Hz, 1H), 2.20 (s, 1H).

Synthesis of the Final Product S10

The synthetic method for S10 is identical to that for S1. The analytical data of S10 are listed as follows: ¹H NMR (300 MHz, CDCl₃) δ 12.21 (s, 0.4H), 12.01 (s, 0.6H), 8.35 (d, J=7.4 Hz, 1H), 7.69 (m, 3H), 7.46-7.28 (m, 2H), 7.02 (t, J=8.7 Hz, 1H), 5.66 (m, 1H), 4.88 (m, 1H), 4.76 (m, 1H), 4.22 (s, 2H), 3.92 (s, 1H), 3.71-3.52 (m, 1H), 3.35 (s, 3H).

11. Synthesis of Compound S11

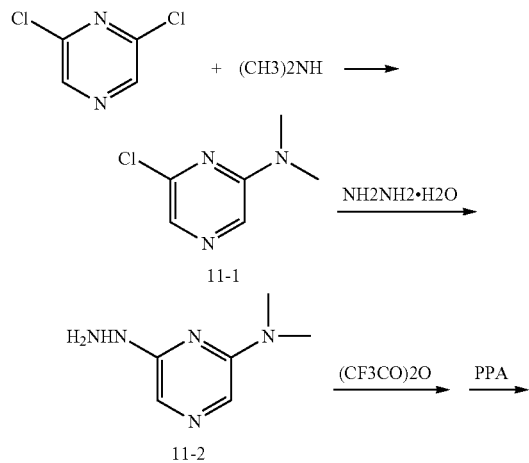

The synthetic methods for final product S11 and its related intermediates are identical to those for S10.

The analytical data of 11-2 are listed as follows: ¹H NMR (300 MHz, DMSO) δ 7.45 (s, 1H), 7.38 (s, 1H), 7.32 (s, 1H), 4.09 (s, 2H), 3.09 (s, 6H).

The analytical data of 11-3 are listed as follows: ¹H NMR (300 MHz, DMSO) δ 9.10 (s, 1H), 8.01 (s, 1H), 3.21 (s, 6H).

The analytical data of 11-4 are listed as follows: ¹H NMR (300 MHz, CDCl₃) δ 5.18 (t, J=7.5 Hz, 1H), 4.18 (d, J=16.8 Hz, 1H), 4.01 (d, J=16.8 Hz, 1H), 3.18 (dd, J=13.5, 3.9 Hz, 1H), 3.03 (d, J=13.5 Hz, 1H), 2.28 (s, 6H), 2.20 (s, 1H).

The analytical data of S11 are listed as follows: ¹H NMR (300 MHz, CDCl₃) δ 12.22 (s, 0.4H), 12.02 (s, 0.6H), 8.33 (d, J=7.4 Hz, 1H), 7.66 (m, 3H), 7.46-7.28 (m, 2H), 7.00 (t, J=8.7 Hz, 1H), 5.26 (m, 1H), 4.86-4.65 (m, 2H), 4.21 (s, 2H), 3.90 (s, 1H), 3.70-3.50 (m, 1H), 2.31 (m, 6H).

12. Synthesis of Compound S12

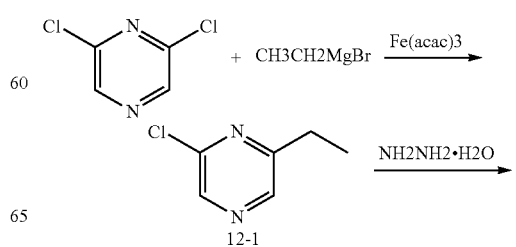

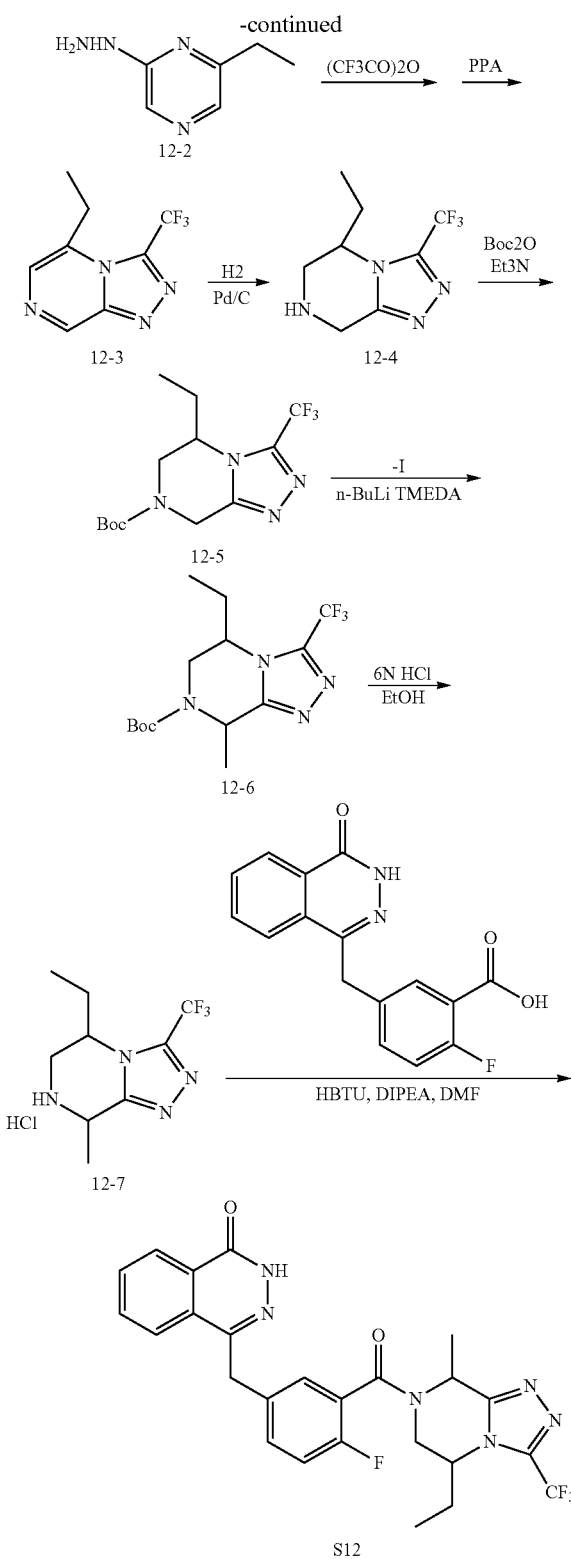

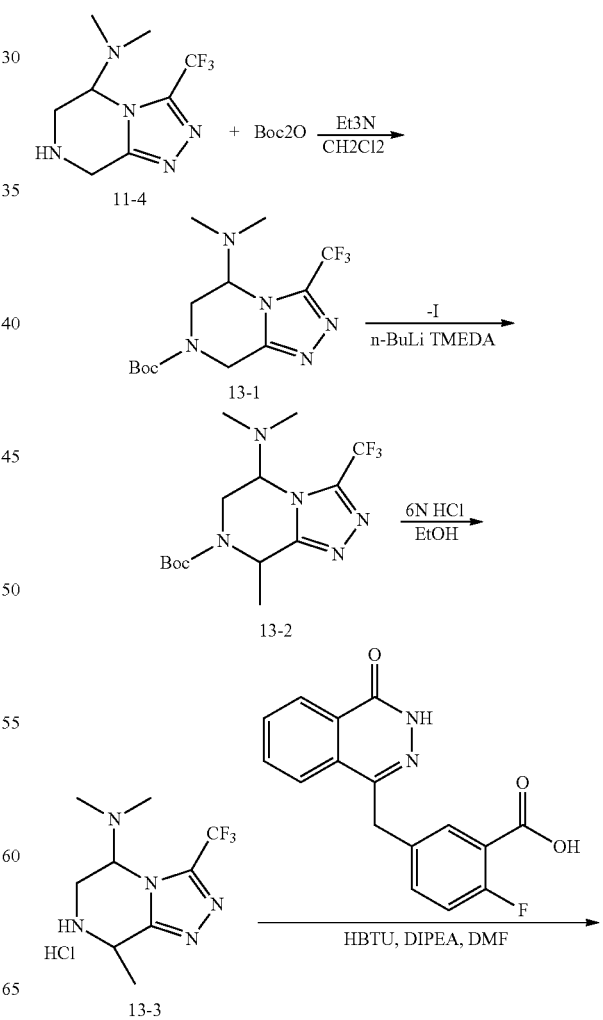

The analytical data of compound 12-2 are listed as follows:
$^1$H NMR (300 MHz, DMSO) δ 7.52 (s, 1H), 7.41 (s, 1H), 7.35 (s, 1H), 4.21 (s, 2H), 3.02 (q, J=7.0 Hz, 2H), 1.10 (t, J=7.0 Hz, 3H).

The analytical data of compound 12-3 are listed as follows:
$^1$H NMR (300 MHz, DMSO) δ 9.01 (s, 1H), 7.92 (s, 1H), 3.03 (q, J=7.0 Hz, 2H), 1.15 (t, J=7.0 Hz, 3H).

The analytical data of compound 12-4 are listed as follows:
$^1$H NMR (300 MHz, CDCl$_3$) δ 4.12 (m, 1H), 4.01 (d, J=16.8 Hz, 1H), 3.83 (d, J=16.8 Hz, 1H), 3.12 (dd, J=13.5, 3.9 Hz, 1H), 2.88 (d, J=13.5 Hz, 1H), 2.20 (s, 1H), 1.75 (q, J=7.0 Hz, 2H), 0.95 (t, J=7.0 Hz, 3H).

The analytical data of compound 12-6 are listed as follows:
$^1$H NMR (300 MHz, CDCl$_3$) δ 5.57 (m, 1H), 4.78-4.16 (m, 2H), 3.29 (m, 1H), 1.73-1.62 (m, 5H), 0.95 (m, 3H).

The analytical data of compound S12 are listed as follows:
$^1$H NMR (300 MHz, CDCl$_3$) δ 11.96 (s, 0.3H), 11.81 (d, J=13.8 Hz, 0.7H), 8.45 (d, J=7.5 Hz, 1H), 7.75 (m, 3H), 7.37 (m, 2H), 7.07 (m, 1H), 6.14 (t, J=6.9 Hz, 0.25H), 5.06 (d, J=7.2 Hz, 0.25H), 4.89 (d, J=14.1 Hz, 0.25H), 4.66 (s, 0.25H), 4.54-4.40 (m, 1H), 4.30-4.28 (m, 2H), 3.81-3.48 (m, 0.5H), 3.48-3.09 (m, 1H), 3.10-3.02 (m, 0.5H), 1.81-1.43 (m, 5H), 0.96 (m, 3H).

13. Synthesis of Compound S13 wherein, intermediate 12-1 was synthesized according to Journal of Natural Products, 2011, 74(7), 1630-1635.

The synthetic method for intermediate 12-4 is identical to that for 11-4, intermediate 12-7 is obtained according to the synthetic method for intermediate 7-3 as described above, and the final product S12 is obtained by a condensation reaction.

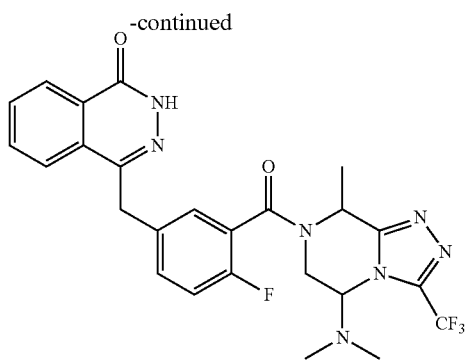

S13

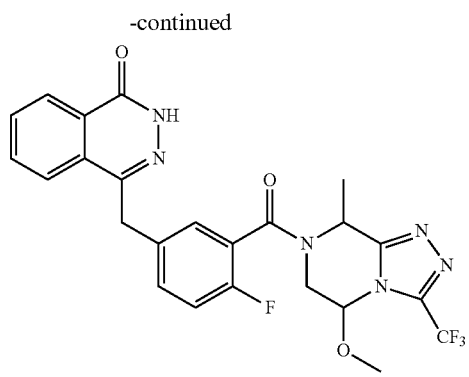

S14

The synthetic method for compound S13 is identical to that for compound S12.

The analytical data of compound S13 are listed as follows: ¹H NMR (300 MHz, CDCl₃) δ 11.83 (s, 0.3H), 11.67 (d, J=13.8 Hz, 0.7H), 8.32 (d, J=7.5 Hz, 1H), 7.59 (m, 3H), 7.21 (m, 2H), 7.01 (m, 1H), 6.15 (m, 0.25H), 5.45 (m, 1H), 5.09-4.85 (m, 0.75H), 4.55-4.39 (m, 2H), 3.79-3.42 (m, 0.5H), 3.46-3.18 (m, 1H), 3.12-3.05 (m, 0.5H), 2.30 (m, 6H), 1.67-1.36 (m, 3H).

The synthetic method for compound S14 is identical to that for compound S12. ¹H NMR (300 MHz, CDCl₃) δ 11.98 (s, 0.3H), 11.80 (d, J=13.8 Hz, 0.7H), 8.47 (d, J=7.5 Hz, 1H), 7.65 (m, 3H), 7.30 (m, 2H), 7.12 (m, 1H), 6.35 (m, 0.25H), 5.87 (m, 1H), 5.15~4.92 (m, 0.75H), 4.64-4.41 (m, 2H), 4.13 (s, 3H), 3.98-3.68 (m, 0.5H), 3.59-3.33 (m, 1H), 3.22-3.12 (m, 0.5H), 1.79-1.51 (m, 3H).

14. Synthesis of Compound S14

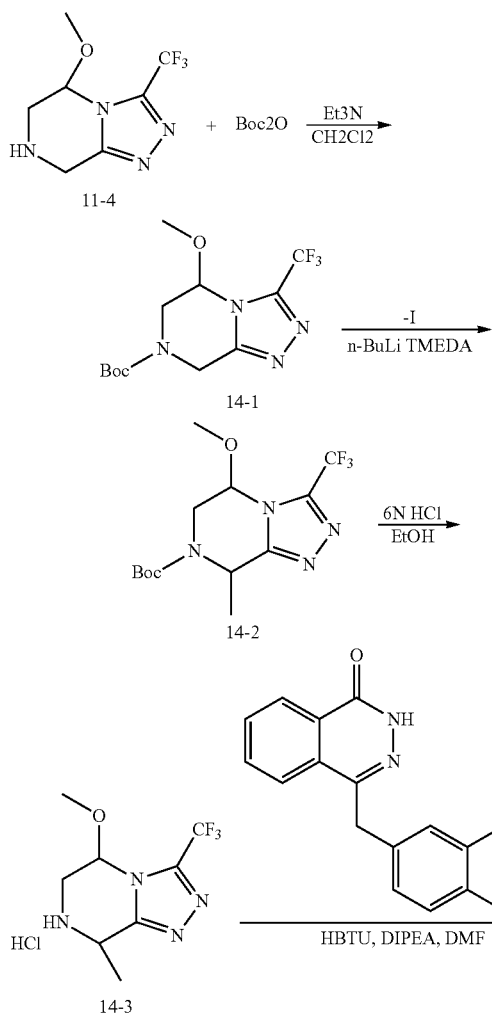

15. Synthesis of Compound S15

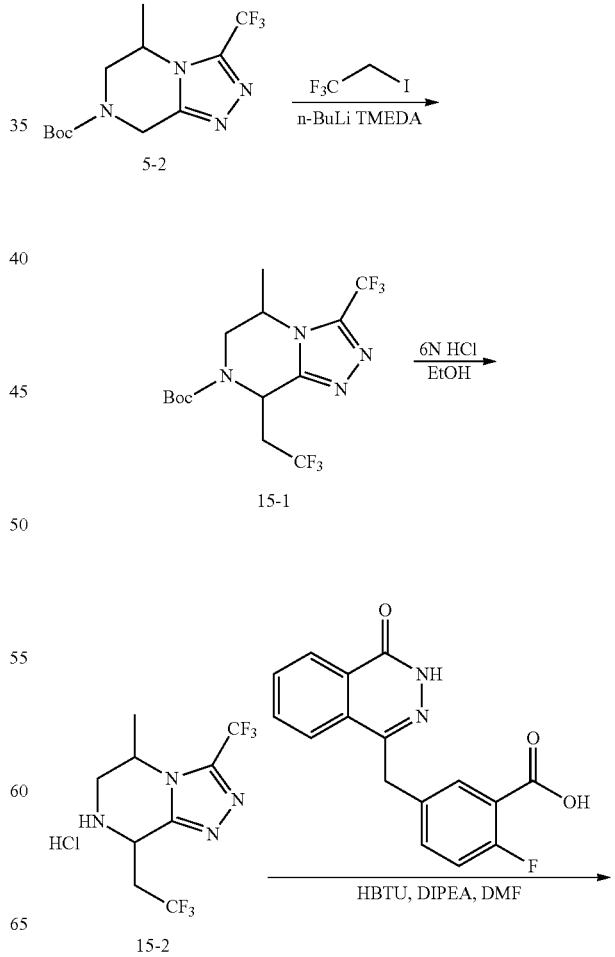

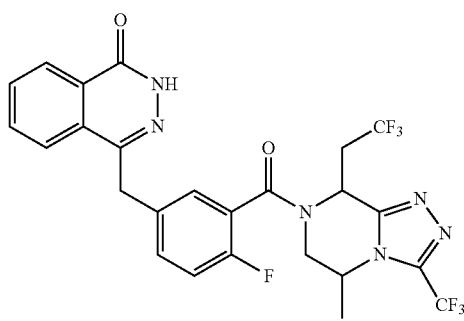

S15

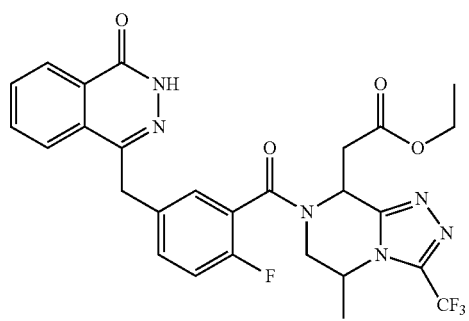

S16

The synthetic method for compound S15 is identical to that for compound S12. $^1$H NMR (300 MHz, CDCl$_3$) δ 12.01 (s, 0.3H), 11.89 (d, J=13.8 Hz, 0.7H), 8.51 (d, J=7.5 Hz, 1H), 7.78 (m, 3H), 7.39 (m, 2H), 7.12 (m, 1H), 6.08 (t, J=6.9 Hz, 0.25H), 5.11 (d, J=7.2 Hz, 0.25H), 4.92 (d, J=14.1 Hz, 0.25H), 4.72 (s, 0.25H), 4.59-4.42 (m, 1H), 4.37-4.27 (m, 2H), 3.92-3.56 (m, 0.5H), 3.51-3.22 (m, 1H), 3.15-3.07 (m, 0.5H), 2.85 (m, 2H), 1.71-1.43 (m, 3H).

The synthetic method for compound S16 is identical to that for compound S12. $^1$H NMR (300 MHz, CDCl$_3$) δ 11.93 (s, 0.3H), 11.79 (d, J=13.8 Hz, 0.7H), 8.43 (d, J=7.5 Hz, 1H), 7.73 (m, 3H), 7.36 (m, 2H), 7.07 (m, 1H), 6.10 (t, J=6.9 Hz, 0.25H), 5.09 (d, J=7.2 Hz, 0.25H), 4.89 (d, J=14.1 Hz, 0.25H), 4.67 (s, 0.25H), 4.55-4.37 (m, 1H), 4.35-4.24 (m, 2H), 3.87-3.53 (m, 0.5H), 3.46-3.18 (m, 1H), 3.12-3.05 (m, 0.5H), 1.71-1.43 (m, 6H).

16. Synthesis of Compound S16

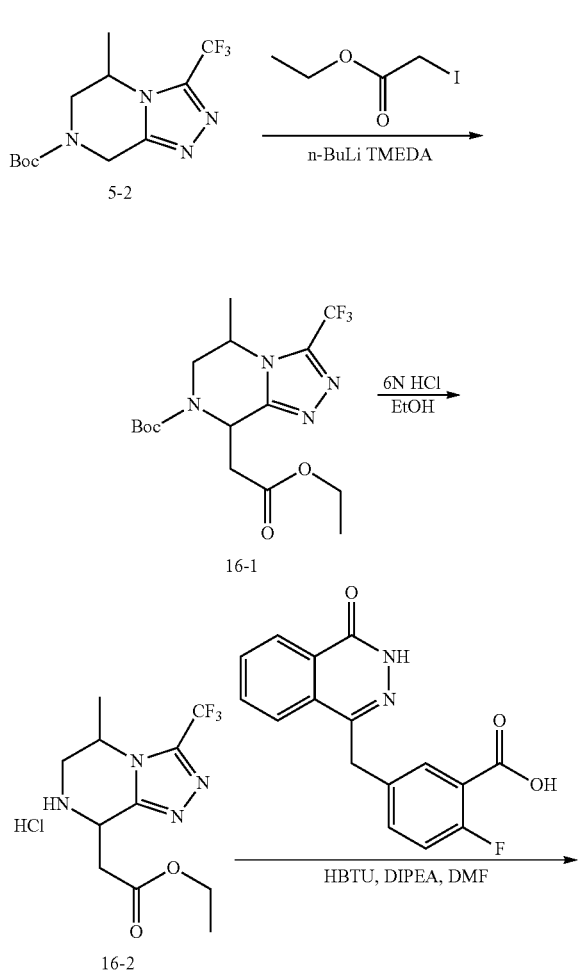

17. Synthesis of Compound S17

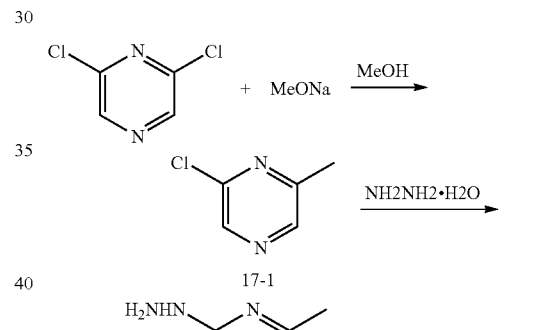

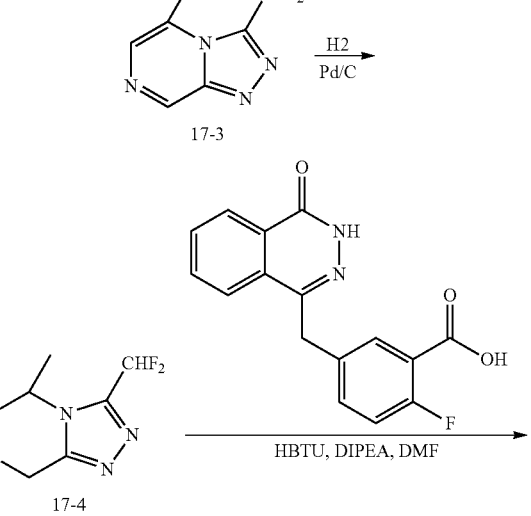

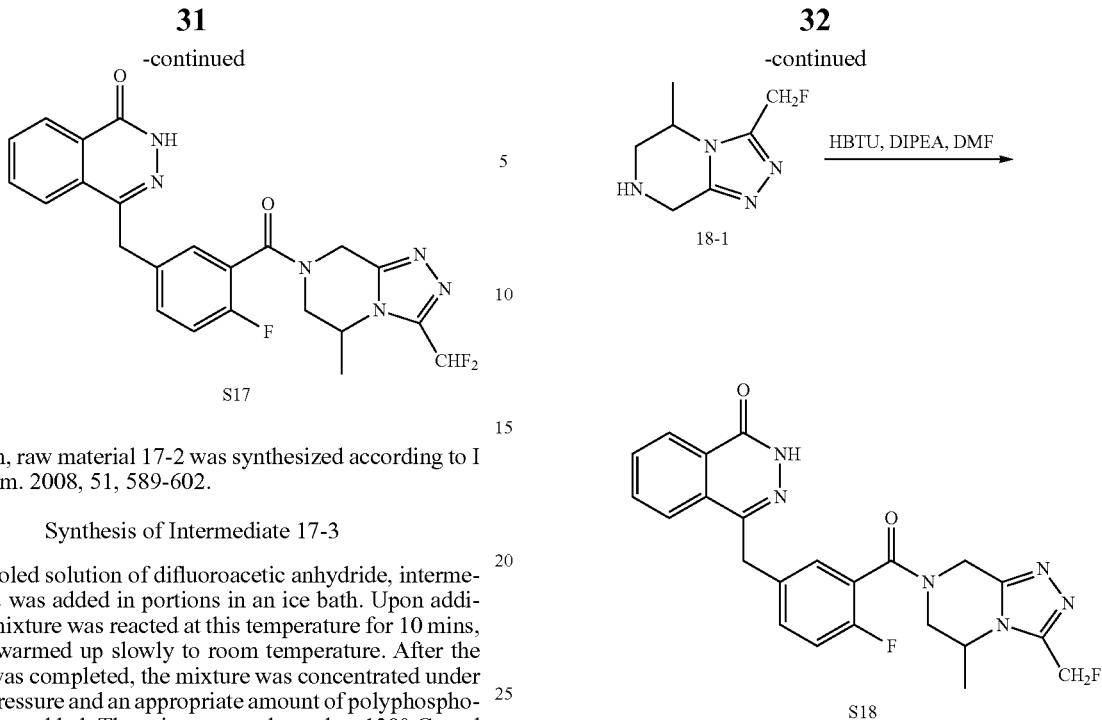

wherein, raw material 17-2 was synthesized according to I Med. Chem. 2008, 51, 589-602.

Synthesis of Intermediate 17-3

To a cooled solution of difluoroacetic anhydride, intermediate 17-2 was added in portions in an ice bath. Upon addition, the mixture was reacted at this temperature for 10 mins, and then warmed up slowly to room temperature. After the reaction was completed, the mixture was concentrated under reduced pressure and an appropriate amount of polyphosphoric acid was added. The mixture was heated to 120° C. and stirred overnight. The reaction solution was cooled, poured into cooled concentrated aqueous ammonia, and filtered to give a crude product 17-3. $^1$H NMR (300 MHz, DMSO) δ 9.51 (s, 1H), 8.08 (s, 1H), 6.87 (t, J=51.6 Hz, 1H), 2.68 (s, 3H).

Synthesis of Intermediate 17-4

Intermediate 17-3 was dissolved in methanol, and an appropriate amount of palladium on carbon was added. The reaction was stirred under hydrogen atmosphere at room temperature overnight. After the reaction was completed, the palladium on carbon residue was filtered off and the filtrate was concentrated to give a crude product 17-4. $^1$H NMR (300 MHz, CDCl$_3$) 66.79 (t, J=51.6 Hz, 1H), 4.57-4.41 (m, 1H), 4.35 (d, J=16.8 Hz, 1H), 4.15 (dd, J=15.9, 7.7 Hz, 1H), 3.22 (dd, J=13.4, 4.0 Hz, 1H), 3.08 (dd, J=13.4, 1.6 Hz, 1H), 2.38-1.98 (m, 1H), 1.54 (t, J=5.9 Hz, 3H).

The synthetic method for the final product S17 is identical to that for S1. $^1$H NMR (300 MHz, CDCl$_3$) δ 12.13 (s, 0.33H), 12.05 (s, 0.67H), 8.34 (d, J=7.4 Hz, 1H), 7.68 (m, 3H), 7.43-7.24 (m, 2H), 6.92-7.08 (m, 2H), 4.85 (m, 1H), 4.74-4.40 (m, 2H), 4.20 (s, 2H), 3.70 (s, 1H), 3.45-3.38 (m, 1H), 1.49 (d, J=6.3 Hz, 3H).

18. Synthesis of Compound S18

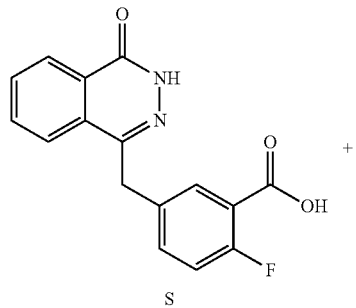

wherein, the synthetic method for fragment 18-1 is identical to that for fragment 17-4. $^1$H NMR (300 MHz, CDCl$_3$) δ 5.47 (d, J=47.9 Hz, 2H), 4.57-4.41 (m, 1H), 4.35 (d, J=16.8 Hz, 1H), 4.15 (dd, J=15.9, 7.7 Hz, 1H), 3.22 (dd, J=13.4, 4.0 Hz, 1H), 3.08 (dd, 0.1=13.4, 1.6 Hz, 1H), 2.38-1.98 (m, 1H), 1.54 (t, J=5.9 Hz, 3H).

The synthetic method for the final product S18 is identical to that for S1. $^1$H NMR (300 MHz, CDCl$_3$) δ 12.13 (s, 0.33H), 12.05 (s, 0.67H), 8.34 (d, J=7.4 Hz, 1H), 7.68 (m, 3H), 7.43-7.24 (m, 2H), 6.92-7.08 (m, 1H), 5.54 (d, J=47.7 Hz, 2H), 4.85 (m, 1H), 4.74-4.40 (m, 2H), 4.20 (s, 2H), 3.70 (s, 1H), 3.45-3.38 (m, 1H), 1.49 (d, J=6.3 Hz, 3H).

19. Synthesis of Compound S19

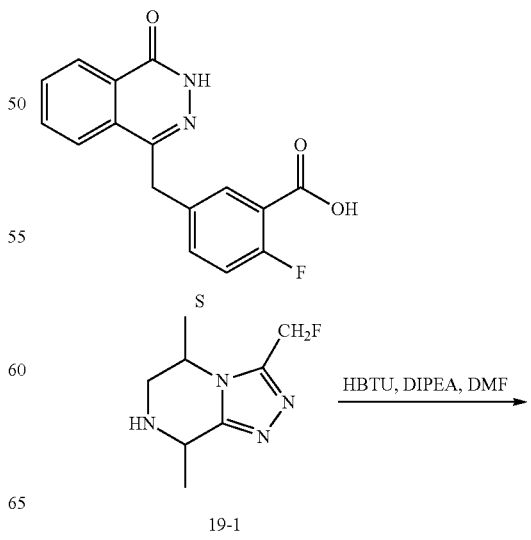

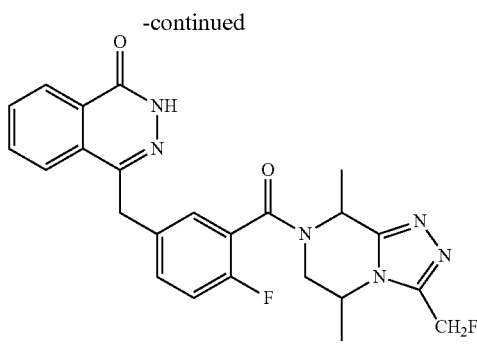

S19 wherein, the synthetic method for fragment 19-1 is identical to that for fragment 5-1. $^1$H NMR (300 MHz, CDCl$_3$) δ 5.59 (s, 1H), 4.73-4.24 (m, 2H), 3.60-3.17 (m, 1H), 2.45 (m, 1H), 1.77-1.58 (m, 6H).

The synthetic method of the final product S19 is identical to that for S1. $^1$H NMR (300 MHz, CDCl$_3$) δ 11.93 (s, 0.3H), 11.79 (d, J=13.8 Hz, 0.7H), 8.43 (d, J=7.5 Hz, 1H), 7.73 (m, 3H), 7.36 (m, 2H), 7.07 (m, 1H), 6.10 (t, J=6.9 Hz, 0.25H), 5.52 (d, J=47.4 Hz, 2H), 5.09 (d, J=7.2 Hz, 0.25H), 4.89 (d, J=14.1 Hz, 0.25H), 4.67 (s, 0.25H), 4.55-4.37 (m, 1H), 4.35-4.24 (m, 2H), 3.87-3.53 (m, 0.5H), 3.46-3.18 (m, 1H), 3.12-3.05 (m, 0.5H), 1.71-1.43 (m, 6H).

20. Synthesis of Compound S20

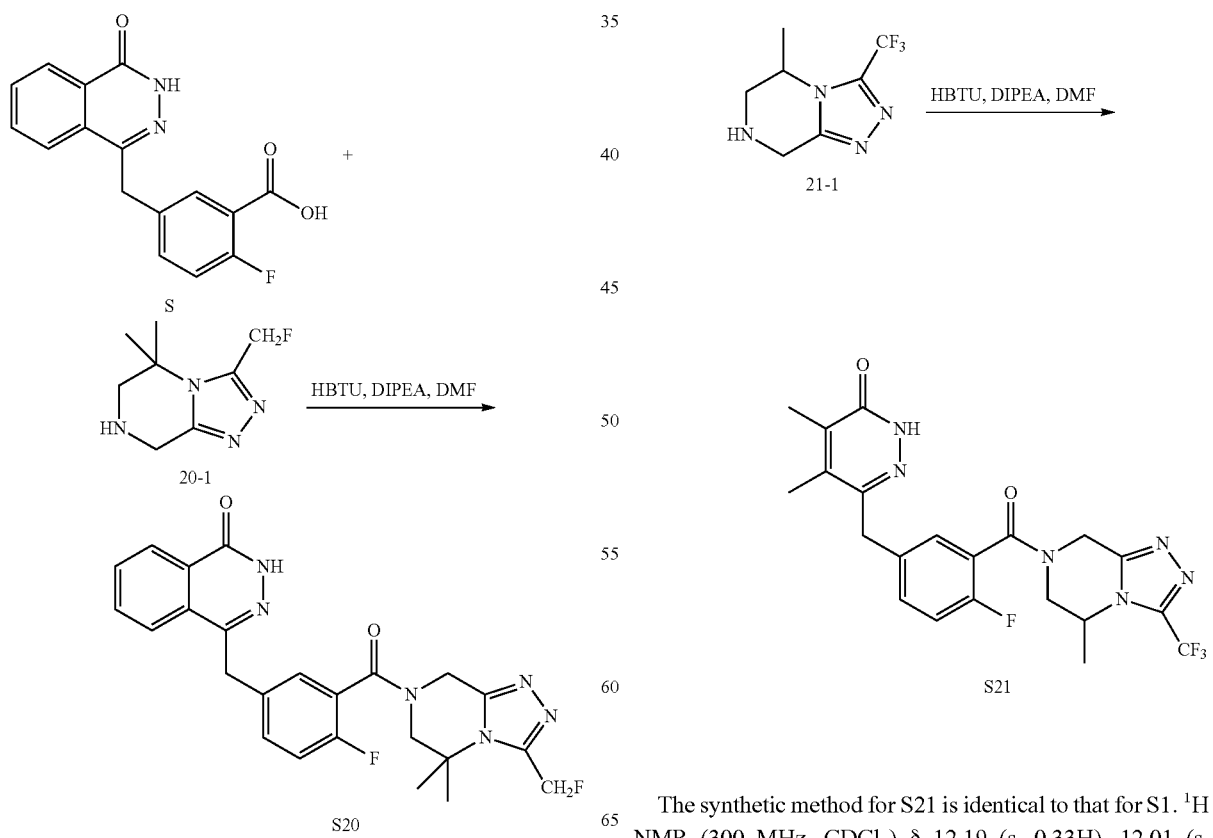

wherein, the synthetic method for fragment 20-1 is identical to that for fragment 6-1. $^1$H NMR (300 MHz, CDCl$_3$) δ 5.48 (d, J=48.3 Hz, 2H), 4.72 (d, J=1.4 Hz, 2H), 3.53 (s, 2H), 2.55 (m, 1H), 1.49 (s, 6H).

The synthetic method for S20 is identical to that for S1. $^1$H NMR (300 MHz, CDCl$_3$) δ 12.11 (s, 0.3H), δ 11.94 (s, 0.7H), 8.39 (d, J=7.2 Hz, 1H), 7.70 (d, J=7.2 Hz, 3H), 7.36 (d, J=5.4 Hz, 2H), 7.03 (t, J=8.7 Hz, 1H), 5.51 (d, J=47.6 Hz, 2H), 5.14 (s, 0.5H), 4.76 (s, 1.5H), 4.27 (s, 2H), 3.98 (s, 1.5H), 3.52 (s, 0.5H), 1.62 (s, 4.35H), 1.40 (s, 1.68H).

21. Synthesis of Compound S21

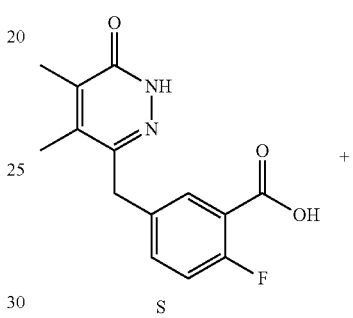

The synthetic method for S21 is identical to that for S1. $^1$H NMR (300 MHz, CDCl$_3$) δ 12.19 (s, 0.33H), 12.01 (s, 0.67H), 7.42 (s, 1H), 7.13 (t, J=8.9 Hz, 1H), 7.01 (d, J=8.7 Hz, 1H), 4.88 (m, 1H), 4.76-4.41 (m, 2H), 4.22 (s, 2H), 3.72 (s, 1H), 3.46-3.41 (m, 1H), 2.44 (s, 3H), 2.14 (s, 3H), 1.49 (d, J=6.3 Hz, 3H).

22. Synthesis of Compound S22

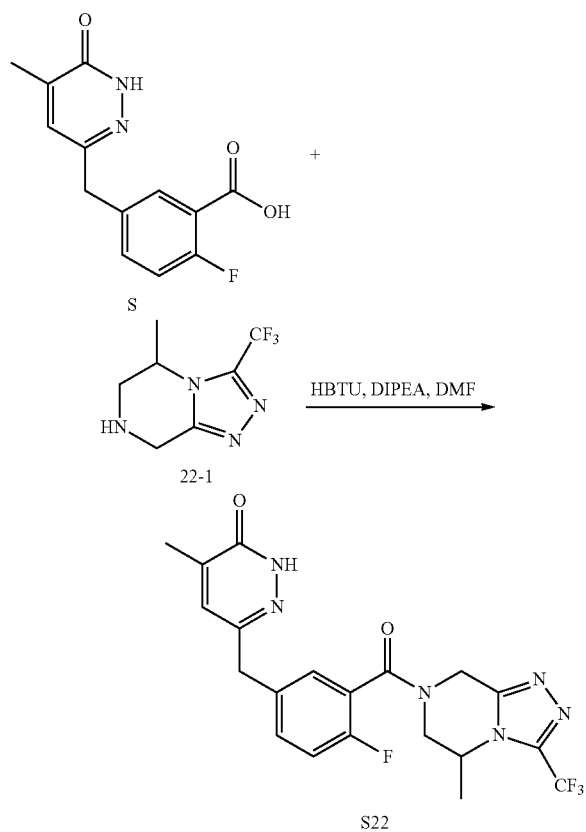

The synthetic method for S22 is identical to that for S1. $^{1}$H NMR (300 MHz, CDCl$_3$) δ 12.19 (s, 0.33H), 12.01 (s, 0.67H), 7.35 (m, 2H), 7.11 (t, J=8.9 Hz, 1H), 6.96 (d, J=8.7 Hz, 1H), 4.88 (m, 1H), 4.76-4.41 (m, 2H), 4.22 (s, 2H), 3.72 (s, 1H), 3.46-3.41 (m, 1H), 2.14 (s, 3H), 1.49 (d, J=6.3 Hz, 3H).

2. Testing Example

1. High Throughput Evaluation of PARP1 Inhibitor at Molecular Level by ELISA

The HTb-PARP1 positive clones were obtained using the full-length PARP1 plasmid, through PCR amplification, enzyme digestion, ligation, and transformation into DH5a. The plasmids were extracted and determined by enzyme cleavage, and then transformed into DH10Bac. Bacmid/PARP is determined by PCR and sequencing. TNI was transfected, the viruses were collected, and cells were lysed. PARP1 protein was purified by affinity chromatography and determined by Western blotting. A plate was coated by substrate histone, NAD$^+$ and DNA, as well as expressed PARP1 enzyme, was placed into 96-well plate reaction system. Various reaction conditions were optimized and ultimately determined. The product PAR was reacted with PAR monoclonal antibody, and then a secondary antibody was added. OD value was read on a microplate reader, and PARP1 enzyme activity inhibition was calculated accordingly, as shown in Table 1.

TABLE 1

PARP1 enzymatic inhibition of compounds at molecular level

| Compound | Structure | molecular level (PARP1) IC$_{50}$ (nM) |
|---|---|---|
| AZD2281 | 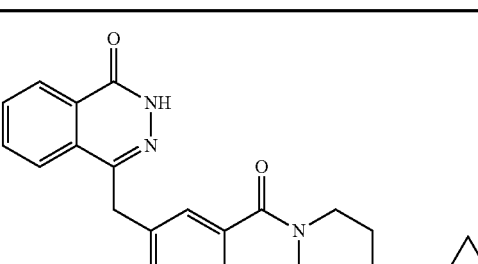 | <50 |

TABLE 1-continued

PARP1 enzymatic inhibition of compounds at molecular level

| Compound | Structure | molecular level (PARP1) IC$_{50}$ (nM) |
|---|---|---|
| S1 | 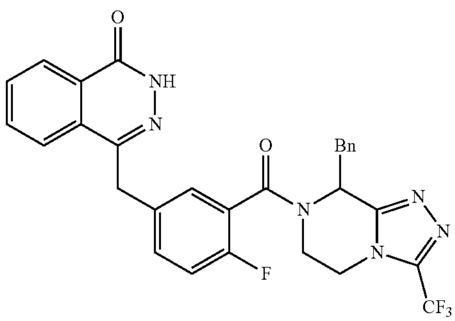 [SMILES: O=C(c1cc(Cc2n[nH]c(=O)c3ccccc23)ccc1F)N1CCn2c(nnc2C(F)(F)F)C1Cc1ccccc1] | 300 |
| S2 | 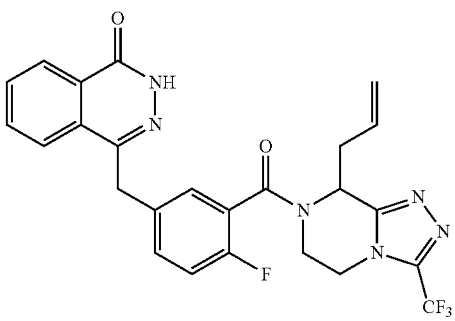 [SMILES: C=CCC1c2nnc(C(F)(F)F)n2CCN1C(=O)c1cc(Cc2n[nH]c(=O)c3ccccc23)ccc1F] | <50 |
| S3 | 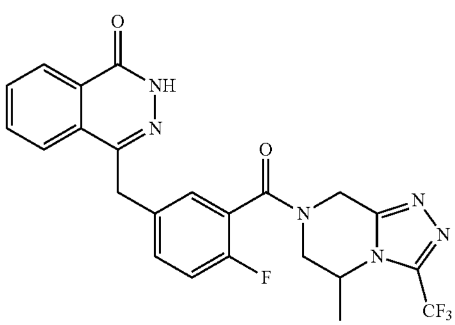 [SMILES: CC1CN(C(=O)c2cc(Cc3n[nH]c(=O)c4ccccc34)ccc2F)Cc2nnc(C(F)(F)F)n21] | <20 |
| S4 | 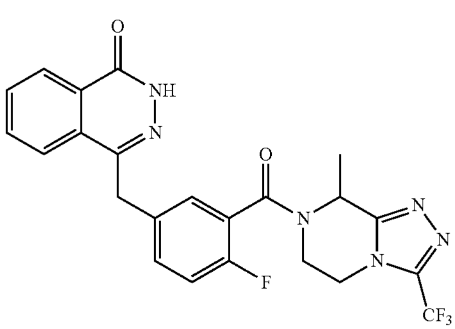 [SMILES: CC1c2nnc(C(F)(F)F)n2CCN1C(=O)c1cc(Cc2n[nH]c(=O)c3ccccc23)ccc1F] | <20 |

TABLE 1-continued

PARP1 enzymatic inhibition of compounds at molecular level

| Compound | Structure | molecular level (PARP1) IC$_{50}$ (nM) |
|---|---|---|
| S5 | 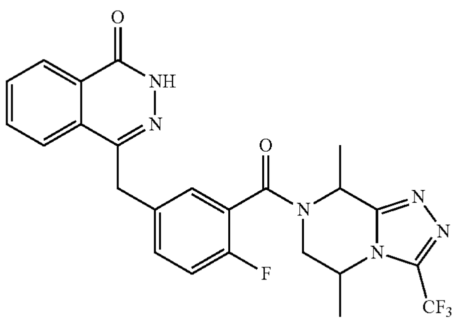 [SMILES: CC1c2nnc(C(F)(F)F)n2C(C)CN1C(=O)c1cc(Cc2n[nH]c(=O)c3ccccc23)ccc1F] | <20 |
| S6 | 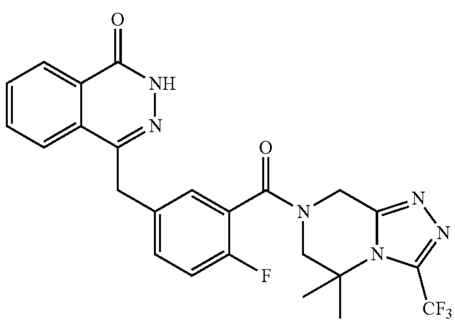 | <50 |
| S7 | 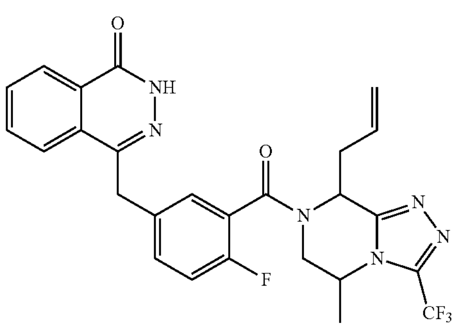 [SMILES: C=CCC1c2nnc(C(F)(F)F)n2C(C)CN1C(=O)c1cc(Cc2n[nH]c(=O)c3ccccc23)ccc1F] | <50 |
| S8 | 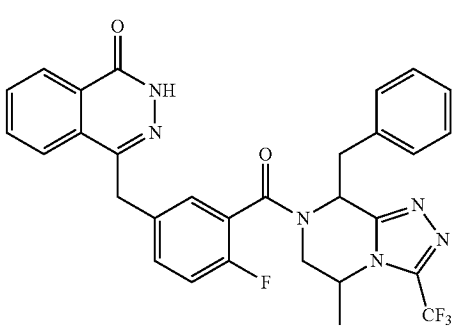 [SMILES: CC1CN(C(=O)c2cc(Cc3n[nH]c(=O)c4ccccc34)ccc2F)C(Cc2ccccc2)c2nnc(C(F)(F)F)n21] | 310 |

TABLE 1-continued

PARP1 enzymatic inhibition of compounds at molecular level

| Compound | Structure | molecular level (PARP1) IC$_{50}$ (nM) |
|---|---|---|
| S9 | 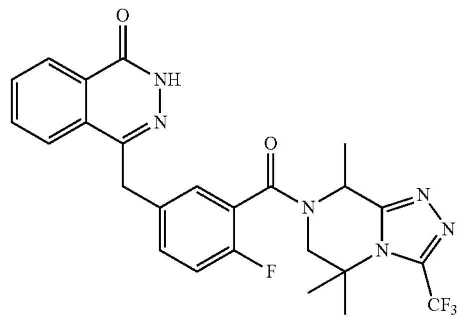 [SMILES: CC1c2nnc(C(F)(F)F)n2C(C)(C)CN1C(=O)c1cc(Cc2n[nH]c(=O)c3ccccc23)ccc1F] | <50 |
| S10 | 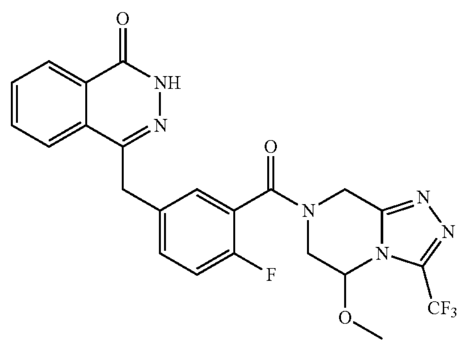 [SMILES: COC1CN(C(=O)c2cc(Cc3n[nH]c(=O)c4ccccc34)ccc2F)Cc2nnc(C(F)(F)F)n21] | <20 |
| S11 | 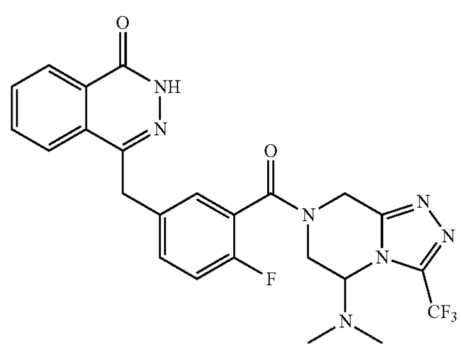 [SMILES: CN(C)C1CN(C(=O)c2cc(Cc3n[nH]c(=O)c4ccccc34)ccc2F)Cc2nnc(C(F)(F)F)n21] | <20 |
| S12 | 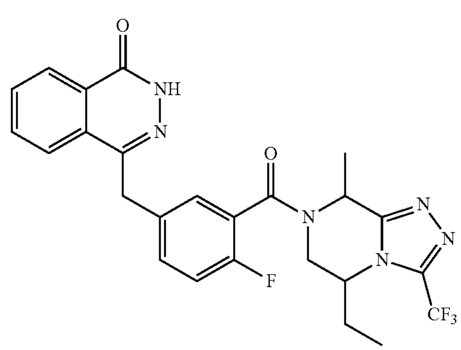 [SMILES: CCC1CN(C(=O)c2cc(Cc3n[nH]c(=O)c4ccccc34)ccc2F)C(C)c2nnc(C(F)(F)F)n21] | <20 |

TABLE 1-continued

PARP1 enzymatic inhibition of compounds at molecular level

| Compound | Structure | molecular level (PARP1) IC$_{50}$ (nM) |
|---|---|---|
| S13 | 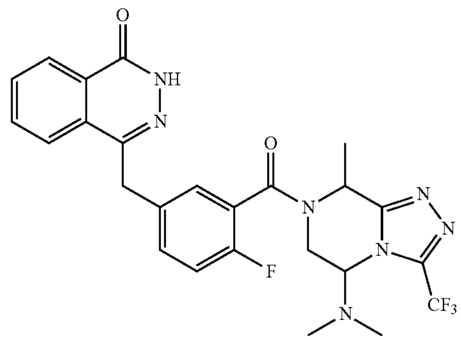 [SMILES: CC1c2nnc(C(F)(F)F)n2C(N(C)C)CN1C(=O)c1cc(Cc2n[nH]c(=O)c3ccccc23)ccc1F] | <50 |
| S14 | 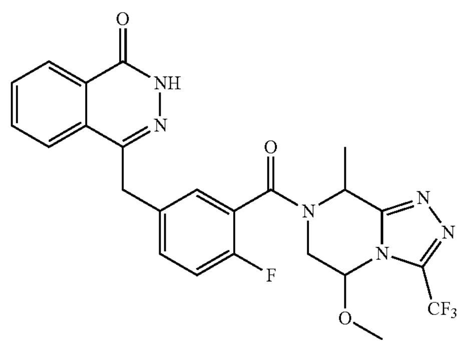 | <50 |
| S15 | 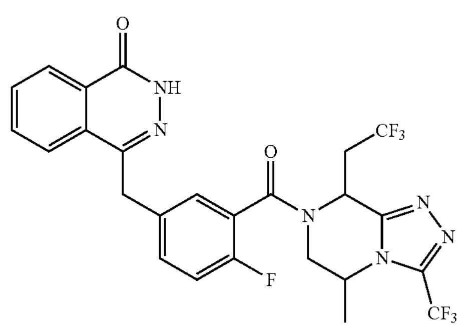 [SMILES: CC1CN(C(=O)c2cc(Cc3n[nH]c(=O)c4ccccc34)ccc2F)C(CC(F)(F)F)c2nnc(C(F)(F)F)n21] | <20 |
| S16 | 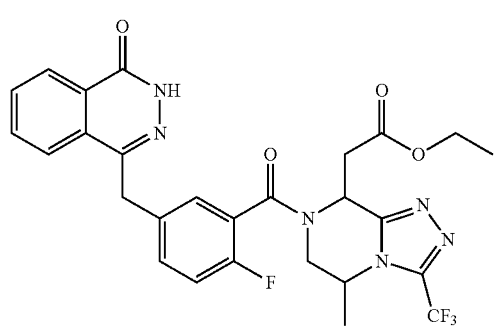 [SMILES: CCOC(=O)CC1c2nnc(C(F)(F)F)n2C(C)CN1C(=O)c1cc(Cc2n[nH]c(=O)c3ccccc23)ccc1F] | <20 |

TABLE 1-continued

PARP1 enzymatic inhibition of compounds at molecular level

| Compound | Structure | molecular level (PARP1) IC$_{50}$ (nM) |
|---|---|---|
| S17 | 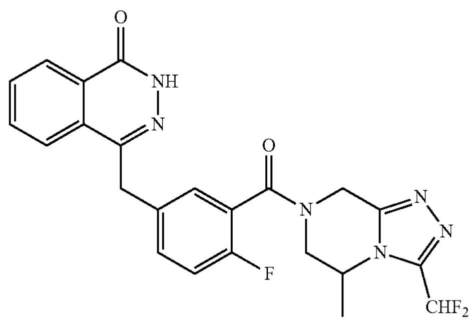 | <20 |
| S18 | 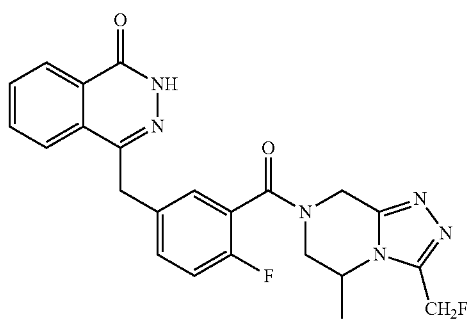 | <20 |
| S19 | 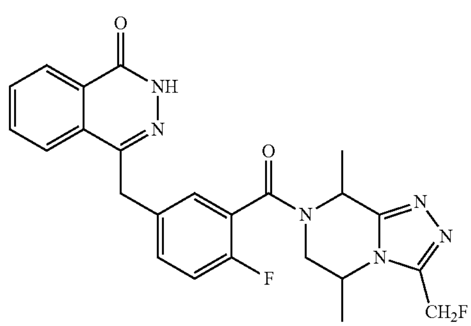 | <50 |
| S20 | 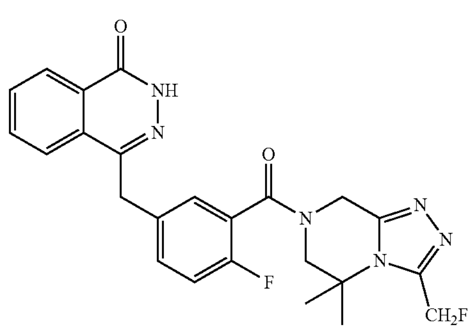 | <20 |

TABLE 1-continued

PARP1 enzymatic inhibition of compounds at molecular level

| Compound | Structure | molecular level (PARP1) IC$_{50}$ (nM) |
|---|---|---|
| S21 | 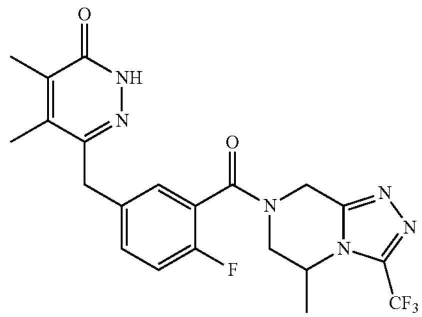 [SMILES: Cc1c(Cc2ccc(F)c(C(=O)N3Cc4nnc(C(F)(F)F)n4C(C)C3)c2)n[nH]c(=O)c1C] | <50 |
| S22 | 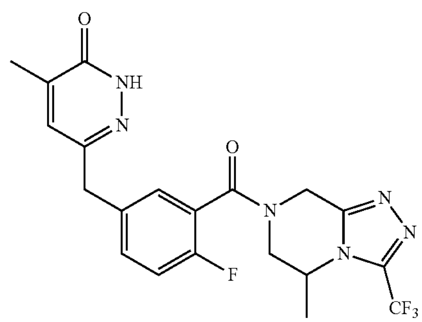 [SMILES: Cc1cc(Cc2ccc(F)c(C(=O)N3Cc4nnc(C(F)(F)F)n4C(C)C3)c2)n[nH]c1=O] | <50 |

It was shown in Table 1 that the majority of compounds exhibited high affinity to PARP1 enzyme at molecular level and exhibited significant inhibitory effect against PARP. The inhibition concentrations for most compounds were in nanomolar range (<100 nM). Some compounds exhibited higher PARP inhibitory activity than the positive compound. The best compound even reached 10 nM or less, and was 13 times more potent than the positive compound AZD-2281. Furthermore, in comparison to the structural characteristics of compounds S1~S16, it was found that the compounds showed different affinity to PARP1 enzyme at molecular level due to the nature and sites of substitution on piperazine ring. For example, S1 and S8 showed very poor affinity (300 nM or so). Therefore, the piperazinotriazole ring and the substituents on the ring have significant contributions to the PARP1 activity.

2. Chiral Separation of Compounds

Since most of the compounds have one or two chiral centers, we separated them by chiral preparative HPLC to get the corresponding optical isomers. For example, both of two enantiomers of compound S3 showed relatively high inhibitory activity to PARP1 enzyme, wherein the activity of (−)-S3 was twice of that of (+)-S3, which means that the (−)-isomer interacts with PARP enzyme more effectively. Specific results were listed as follows:

1) Chiral Resolution Conditions:

Chiral column: CHIRALPAK IA

Chiral column size: 0.46 cm I.D.×15 cm L

Mobile phase: Hexane/IPA=40/60 (v/v); flow rate: 1 ml/min

Detection wavelength: UV 254 nm

Figure 2:
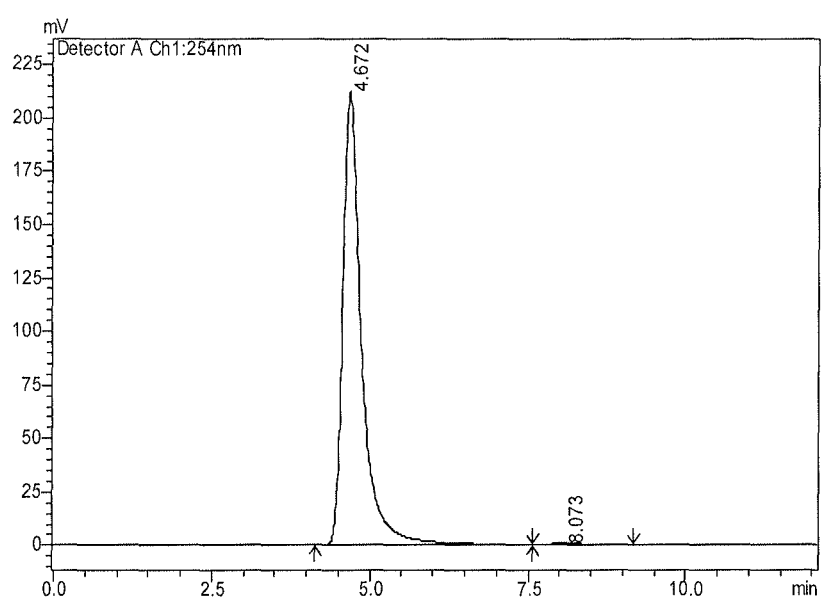
FIG. 2 is a spectrum of optical isomer S3-(+).
Figure 3:
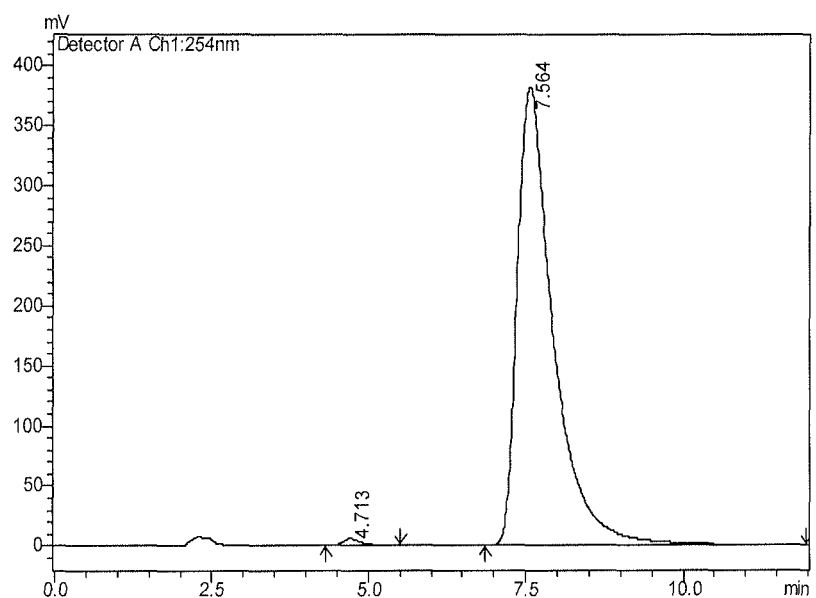
FIG. 3 is a spectrum of optical isomer S3-(−).

2) Chiral HPLC spectrum: Referring to FIGS. 1-3.

3) PARP1 Inhibitory Activity of Enantiomers:

TABLE 2
PARP1 inhibitory activity of S3 and its corresponding enantiomers
| Compound | Structure | Optical rotation value $[\alpha]^{20}D$ | molecular level (PARP1) $IC_{50}$ (nM) |
|---|---|---|---|
| AZD2281 | 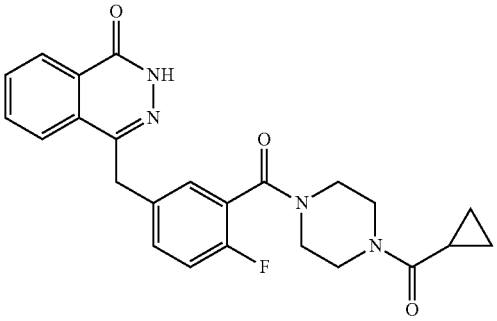 [SMILES: O=C(c1cc(Cc2n[nH]c(=O)c3ccccc23)ccc1F)N1CCN(C(=O)C2CC2)CC1] | none | 43 |
| S3 | 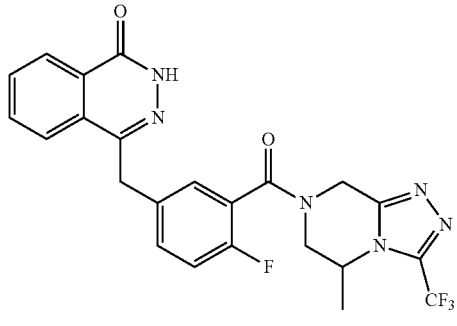 [SMILES: CC1CN(C(=O)c2cc(Cc3n[nH]c(=O)c4ccccc34)ccc2F)Cc2nnc(C(F)(F)F)n21] | none | 10 |
| S3-(+) | 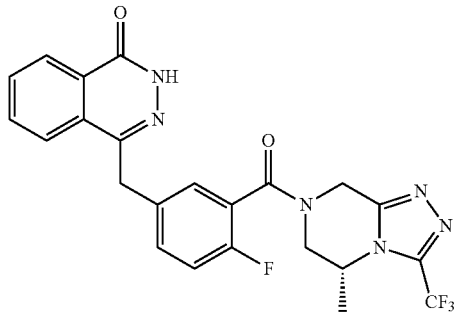 [SMILES: C[C@@H]1CN(C(=O)c2cc(Cc3n[nH]c(=O)c4ccccc34)ccc2F)Cc2nnc(C(F)(F)F)n21] | 5.4 (c 0.48, CHCl3) | 15 |
| S3-(−) | 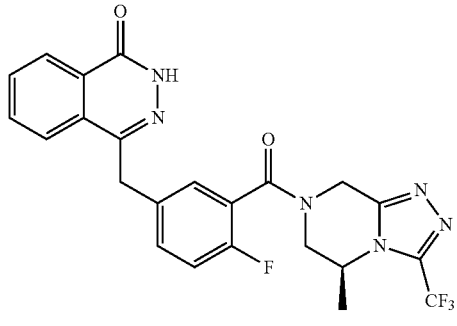 [SMILES: C[C@H]1CN(C(=O)c2cc(Cc3n[nH]c(=O)c4ccccc34)ccc2F)Cc2nnc(C(F)(F)F)n21] | −7.2 (c 0.46, CHCl3) | 7 |

3. Cellular Assay of Representative Compounds

Based on the preliminary PARP1 inhibition evaluation of compounds at molecular level by ELISA, compounds were further evaluated for their cellular inhibition against PARP1 using a proliferation inhibition model, and the results were shown as follows:

TABLE 3

PARP1 inhibitory activity of compounds at cellular level

| Compound | PARP1 inhibitory activity at cellular level (%; nM) | | | | | $IC_{50}$ (nM) |
|---|---|---|---|---|---|---|
| | 1000 | 200 | 40 | 8 | 1.60 | |
| S3 | 74.43 | 70.14 | 61.19 | 33.08 | −3.11 | 17.33 |
| S4 | 75.65 | 75.50 | 53.12 | 8.66 | −1.36 | 35.52 |
| S5 | 73.53 | 63.78 | 23.48 | −3.01 | −5.06 | 98.74 |
| S10 | 78.59 | 67.54 | 31.82 | 10.51 | 11.62 | 83.97 |
| S17 | 79.72 | 76.50 | 65.60 | 12.12 | 4.61 | 24.77 |
| S18 | 78.44 | 77.03 | 76.98 | 54.12 | 7.63 | 7.15 |
| S19 | 0.69 | 0.40 | 3.32 | −2.17 | 2.09 | — |
| AZD2281 | 81.321 | 67.977 | 31.49 | 9.079 | −3.57 | 86.32 |

\* negative value means that there is no inhibition on proliferation, and can be regarded as zero; similar for others.

From the above results, it was showed that new compounds not only had higher activity at the PARP1 enzyme, but also exhibited significant activity against V8 cell directly related to PARP1, wherein the activity of some compounds was 12 times of that of the positive compound AZD2281.

4. Comparison of the Inhibitory Effects of Representative Compound S3 and AZD2281 on Different Tumor Cells Proliferation In order to determine the potential advantage of new compounds over AZD2281, the antiproliferative effects of representative compound S3 on different tumor cells was tested and compared with that of AZD2281. Results were shown in Table 4. It was showed that the inhibition of S3 on tumor cells from four different tissues was universally higher than that of AZD2281, with 178 times higher potency at the most.

TABLE 4 inhibition of representative compound S3 and AZD2281 on different tumor proliferation

| Cell strain | Tumor type | $IC_{50}$ (nM) S3 | $IC_{50}$ (nM) AZD2281 | ratio $IC_{50\,AZD}/IC_{50\,S3}$ |
|---|---|---|---|---|
| Capan-1 | pancreatic cancer | 7.6 | 729 | 95.9 |
| PC-3 | prostatic carcinoma | 995 | 3922 | 3.9 |
| U87-MG | neuroglioma | 228 | 2922 | 12.8 |
| U251 | neuroglioma | 6.7 | 1194 | 178 |
| OVCAR-8 | ovarian cancer | 10500 | 12360 | 1.2 |

5. Selectivity of Representative Compound S3 for Enzyme of PARP Family

In order to test the selectivity of substituents on piperazinotriazole ring within the PARP family, the selectivity of compound S3 and positive compound AZD2281 were tested. Results were shown in following table.

TABLE 5 the selectivity of compounds for PARP subtypes

| PARPs | $IC_{50}$(nM) | | Ratio 1* | | Ratio 2** | |
|---|---|---|---|---|---|---|
| | S3 | AZD2281 | S3 | AZD2281 | S3 | AZD2281 |
| PARP1 | 0.74 nM | 0.9 nM | 1 | 1 | — | — |
| PARP2 | 0.22 nM | 0.45 nM | — | — | 1 | 1 |
| PARP3 | 66.9 nM | 320 nM | 90.4 | 340.4 | 304.1 | 711.1 |
| TNKS1 | 650 nM | 10.4 nM | 878.4 | 11.1 | 2954.5 | 23.1 |
| TNKS2 | 930 nM | 5.2 nM | 1256.8 | 5.5 | 4227.3 | 11.6 |
| PARP6 | 372 nM | 1,700 nM | 502.7 | 1808.5 | 1690.9 | 3777.8 |

*the ratio of $IC_{50}$ of the corresponding compound on other subtype to $IC_{50}$ on PARP1
**the ratio of $IC_{50}$ of the corresponding compound on other subtype to $IC_{50}$ on PARP1

It was shown in the above table that the newly synthesized substituted piperazinotriazole derivative S3 had significantly higher activity on PARP1 and PARP2 than the positive compound. Meanwhile, compound S3 showed higher selectivity, especially over TNKS1 and TNKS2 the selectivity reached 870 times or more, while the positive compound showed lower selectivity over the two subtypes, which was only 5.5-23.1 times. The function of TNKS1 and TNKS2 is not well known yet, so the poor selectivity of the positive compound for them may result in high risk of unpredictable toxicity. Therefore, compared with the positive compound AZD2281, the newly synthesized compound (S3) obviously exhibited higher selectivity for PARP1/2, thus possessing lower risk of unpredictable toxicity.

5. Inhibitory Activity of Compounds on Potassium Channels hERG

In order to evaluate whether a new compound has better safety concerns, particularly, the inhibitory activity on potassium channels hERG related to heart toxicity, the inhibitory effects of these compounds on hERG were tested. Results were shown in following table.

TABLE 5 inhibition of compounds on potassium channels hERG

| Compound | IC50(μM) |
|---|---|
| S1 | >10 |
| S3 | >10 |
| S3-(+) | >10 |
| S3-(−) | >10 |
| S7 | >10 |
| S10 | >10 |
| S15 | >10 |
| S17 | >10 |

It was shown that these compounds, either as racemate or as a single stereoisomer, had no inhibition on potassium channels hERG, so they had lower risk of heart toxicity.

6. Antitumor Activity of Representative Compound S3 In Vivo

A tumor tissue in vigorous growing period was cut into about 1.5 mm³, and inoculated subcutaneously into right armpit of nude mice under a sterile condition. The diameter of subcutaneous transplant tumor in nude mice was measured by vernier caliper. When the tumor grew to 100-200 mm³, the animals were randomly grouped. S3 was administered in 100 mg/kg and 25 mg/kg and positive drug AZD2281 was administered in 100 mg/kg, which were administered orally once a day, for three weeks successively. Solvent control group was administered saline in same volume. During the whole experiment, the tumor diameter was measured twice a week, while the body weight of mice was weighed simultaneously. The formula to calculate tumor volume (TV) was TV=½*a*b², wherein a and b respectively referred to length and width. Relative tumor volume (RTV) was calculated according to the measurements, and the formula is RTV=Vt/V0, wherein V0 is the tumor volume measured when the mice were grouped (i.e. d0), and Vt is the tumor volume measured each time. Index for evaluating antitumor activity is: 1) relative tumor proliferation rate T/C (%), the calculation formula of which is as follows: T/C (%)=($T_{RTV}$/$C_{RTV}$)×100%, $T_{RTV}$: RTV of treatment group; $C_{RTV}$: RTV of negative control group; 2) inhibition rate of tumor volume growth GI %, the calculation formula of which is as follows: GI %=[1−(TVt−TV0)/(CVt−CT0)]×100%, $TV_t$ is the tumor volume measured each time in treatment group; $TV_0$ is the tumor volume measured when the mice were grouped in treatment group; $CV_t$ is the tumor volume measured each time in control group; and $CV_0$ is the tumor volume measured when the mice were grouped in control group; 3) inhibition rate of tumor weight, the calculation formula of which is as follows: inhibition rate of tumor weight %=(We−WT)/Wc×100%, We is the tumor weight in control group, WT is the tumor weight in treatment group.

The results were shown in Table 6. Compound S3, when administered orally at doses of 100 mg/kg and 25 mg/kg once a day for 21 days successively, showed significant subcutaneously transplanted tumor growth inhibition in MDA-MB-436 human breast cancer nude mice, and the T/C (%) was respectively 0.59% and 9.80% on 21th day. In 25 mg/kg group, antitumor activity of S3 is equal to that of the positive control AZD2281; while in 100 mg/kg group, antitumor activity of S3 is much higher than that of the positive control AZD2281.

TABLE 6

Therapeutic effect of S3 on transplanted tumor in MDA-MB-436 human breast cancer nude mice

| Group | Dose, asministration | Animal No. $d_0$ | Animal No. $d_{21}$ | TV (mm³) (mean ± SD) $d_0$ | TV (mm³) (mean ± SD) $d_{21}$ | RTV (mean ± SD) | T/C (%) |
|---|---|---|---|---|---|---|---|
| Solvent control | 0.2 ml per animial, qd × 21 | 12 | 12 | 125 ± 24 | 1698 ± 672 | 14.26 ± 7.74 | |
| S3 | 100 mg/kg, po qd × 21 | 6 | 6 | 128 ± 36 | 11 ± 7(1) | 0.08 ± 0.04** | 0.59 |
| | 25 mg/kg, po qd × 21 | 6 | 6 | 127 ± 30 | 165 ± 57(3) | 1.40 ± 0.71** | 9.80 |
| AZD2281 | 100 mg/kg, po qd × 21 | 6 | 6 | 127 ± 37 | 120 ± 118 | 0.95 ± 0.78** | 6.65 |

**$p < 0.05$; the number in "( )" is the number of animals in which tumor regressed In summary, compound S3 has significant anti-tumor activity in vivo; at the dose of 25 mg/kg, the tumor growth inhibition of S3 is equal to that of positive compound at the dose of 100 mg/kg. At the dose of 100 mg/kg, the tumor completely disappeared. More importantly, at both doses, compound S3 showed no significant side effects.

In summary, such piperazinotriazole compounds containing one or more substituents represented by compound S3 have extremely high inhibitory activity against PARP1 enzyme, and their cellular antiproliferative activity is significantly higher than the positive compound AZD2281 as well. Meanwhile, the substituents on ring remarkably improved the selectivity of compounds on telomerase, TNKS1 and TNKS2, resulting in low risk of cardiac toxicity. The tumor growth inhibition of new compounds on the PARP1-related xenograft mice models is significantly higher than that of the positive compound. Therefore, these compounds represent novel highly selective poly ADP-ribose polymerase-1 (PARP1) inhibitors and can be used for the prevention and/or treatment of PARP related diseases.

The invention claimed is:
1. A compound of formula I, or a pharmaceutically acceptable salt, stereoisomer, tautomer or ester thereof:

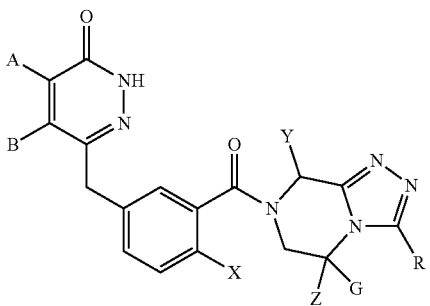

wherein each of A and B independently is a hydrogen, a substituted or unsubstituted C1-C8 alkyl, a substituted or unsubstituted C2-C8 alkenyl or a substituted or unsubstituted C2-C8 alkynyl; wherein the substituent for substitution is selected from the group consisting of a halogen, a cyano, a nitro, a hydroxy and an amino; with the proviso that A and B are not both hydrogen; or A and B, together with the carbon atoms to which they are connected, form a substituted or unsubstituted C4-C8 aliphatic ring, a substituted or unsubstituted C6-C10 aromatic ring, a substituted or unsubstituted 4-8 membered heterocyclic ring containing one to three atoms selected from N, O or S, or a substituted or unsubstituted 5-8 membered heteroaromatic ring containing one to three atoms selected from N, O or S; wherein the substituent for substitution is selected from the group consisting of a halogen, a cyano, a nitro, a hydroxy and an amino;

X is a hydrogen, a halogen, a hydroxy or a cyano,

Y is a hydrogen or a substituted or unsubstituted C1-C8 alkyl; wherein the substituent for substitution is selected from the group consisting of a halogen, a cyano, a nitro, a hydroxy, an amino, a C1-C6 alkoxy, a C2-C6 alkyl carbonyl, a C2-C6 alkoxy carbonyl, a C2-C6 alkenyl, a C2-C6 alkynyl and a C6-C10 aryl, G is a hydrogen, a C1-C6 alkyl, a C1-C6 alkoxy, a C2-C6 alkyl carbonyl, a C1-C6 alkyl amino or a (C1-C6 alkyl)$_2$ amino, Z is a hydrogen, a C1-C6 alkyl, a C1-C6 alkoxy, a C2-C6 alkyl carbonyl, a C1-C6 alkyl amino or a (C1-C6 alkyl)$_2$ amino, with the proviso that Y, G and Z are not all hydrogen, and R is selected from a hydrogen or a substituted or unsubstituted C1-C8 alkyl; wherein the substituent for substitution is selected from a group consisting of a halogen, a cyano, a nitro, a hydroxy, an amino, a C1-C6 alkoxy, a C2-C6 alkyl carbonyl, a C2-C6 alkoxy carbonyl and a C6-C10 aryl.

2. The compound of claim 1, wherein:

each of A and B is independently a hydrogen, a substituted or unsubstituted C1-C8 alkyl, a substituted or unsubstituted C2-C8 alkenyl, or a substituted or unsubstituted C2-C8 alkynyl, or A and B, together with the carbon atoms to which they are connected, form a substituted or unsubstituted C4-C7 aliphatic ring, a substituted or unsubstituted C6-C8 aromatic ring, a substituted or unsubstituted 4-7 membered heterocyclic ring containing one to three atoms selected from N, O or S, or a substituted or unsubstituted 5-7 membered heteroaromatic ring containing one to three atoms selected from N, O or S.

3. The compound of claim 2, wherein;

each of A and B is independently a hydrogen or a substituted or unsubstituted C1-C6 alkyl; or A and B, together with the carbon atoms to which they are connected, form a substituted or unsubstituted C4-C7 aliphatic ring or a substituted or unsubstituted C6-C8 aromatic ring; and R is a hydrogen or a substituted or unsubstituted C1-C6 alkyl, wherein the substituent for substitution is selected from a group consisting of a halogen, a cyano, a nitro, a hydroxy and an amino.

4. The compound of claim 3, wherein:

each of A and B is independently a hydrogen or a C1-C4 alkyl, or or, A and B, together with the carbon atoms to which they are connected, form a substituted or unsubstituted C4-C6 aliphatic ring, a substituted or unsubstituted C6-C8 aromatic ring, in which the substituent for substitution is selected from a group consisting of a halogen, a cyano, a nitro, a hydroxy and an amino, Y is a hydrogen or a substituted or unsubstituted C1-C4 alkyl, and the substituent for substitution is selected from a group consisting of a halogen, a cyano, a nitro, a hydroxy, an amino, a C1-C4 alkoxy, a C2-C4 alkoxy carbonyl, a C2-C4 alkenyl, and a phenyl, G is a hydrogen, a C1-C4 alkyl, a C1-C4 alkoxy, a C1-C4 alkyl amino or a (C1-C4 alkyl)$_2$ amino, Z is a hydrogen, a C1-C4 alkyl, a C1-C4 alkoxy, a C1-C4 alkyl amino or a (C1-C4 alkyl)$_2$ amino, and R is a hydrogen and a substituted or unsubstituted C1-C4.

5. The compound of claim 4, wherein:

each of A and B is independently a hydrogen or a methyl, or

A and B, together with the carbon atoms to which they are connected, form a phenyl, X is a hydrogen or a halogen;

Y is a hydrogen, a methyl, a 2,2,2-trifluoroethyl, an allyl, an ethoxy carbonyl ethyl or a benzyl, G is a hydrogen, a methyl, an ethyl, a methoxy or a dimethyl amino, Z is a hydrogen, a methyl, an ethyl, a methoxy or a dimethyl amino, and R is a hydrogen, a fluoromethyl, a difluoromethyl or a trifluoromethyl.

6. The compound of claim 1, wherein

Y is a substituted or unsubstituted C1-C8 alkyl, in which the substituent for substitution is selected from a group consisting of a halogen, a cyano, a nitro, a hydroxy, an amino, a C1-C6 alkoxy, a C2-C6 alkyl carbonyl, a C2-C6 alkoxy carbonyl, a C2-C6 alkenyl, a C2-C6 alkynyl and a C6-C10 aryl.

7. The compound of claim 1, wherein, when G is a hydrogen, Z is a C1-C6 alkyl, a C1-C6 alkoxy, a C2-C6 alkyl carbonyl, a C1-C6 alkyl amino or a (C1-C6 alkyl)$_2$ amino, or when Z is a hydrogen, G is a C1-C6 alkyl, a C1-C6 alkoxy, a C2-C6 alkyl carbonyl, a C1-C6 alkyl amino or a (C1-C6 alkyl)$_2$ amino.

8. The compound of claim 1, wherein G is a C1-C6 alkyl, a C1-C6 alkoxy, a C2-C6 alkyl carbonyl, a C1-C6 alkyl amino or a (C1-C6 alkyl)$_2$ amino.

9. The compound of claim 1, wherein Z is a C1-C6 alkyl, a C1-C6 alkoxy, a C2-C6 alkyl carbonyl, a C1-C6 alkyl amino or a (C1-C6 alkyl)$_2$ amino.

10. The compound of claim 1, wherein the compound is one of the following compounds:

(S1) 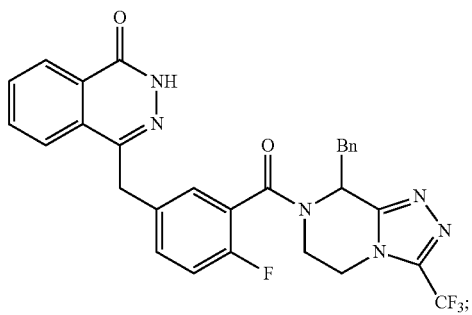
(S6) 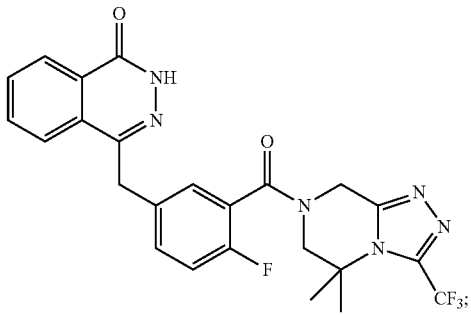
(S2) 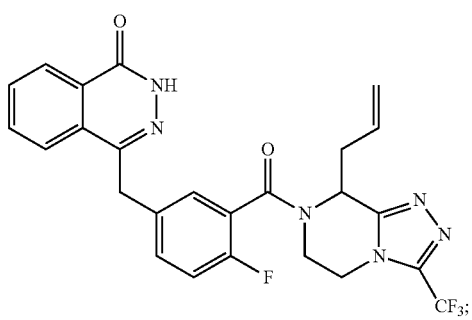
(S7) 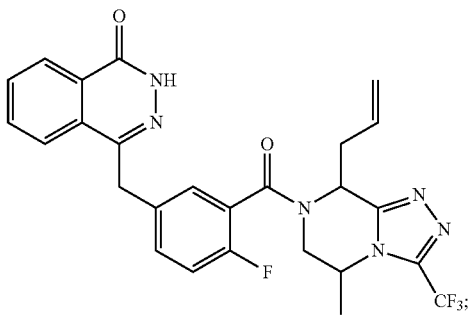
(S3) 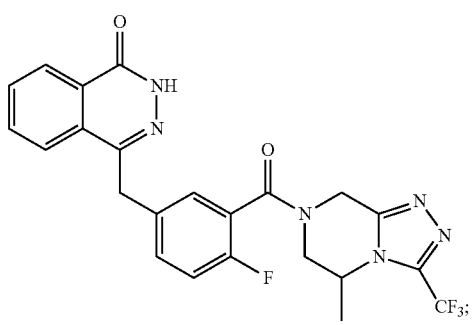
(S8) 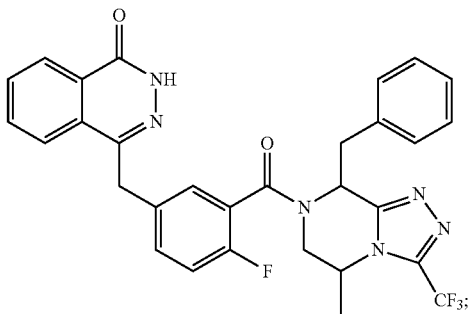
(S4) 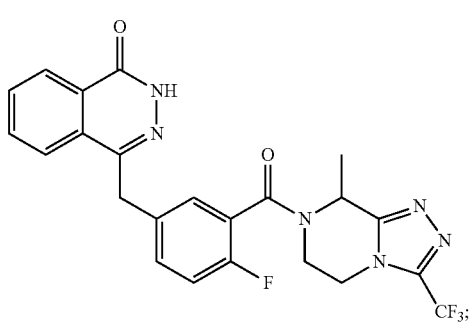
(S9) 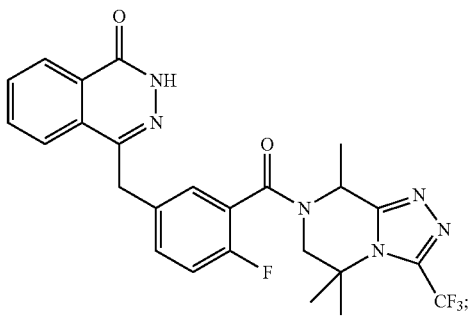
(S5) 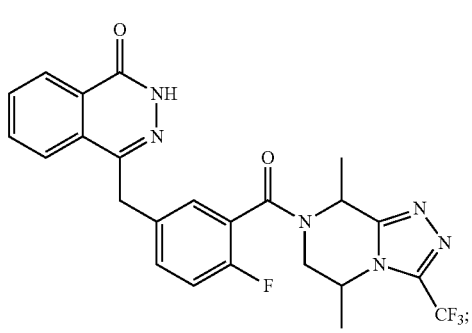
(S10) 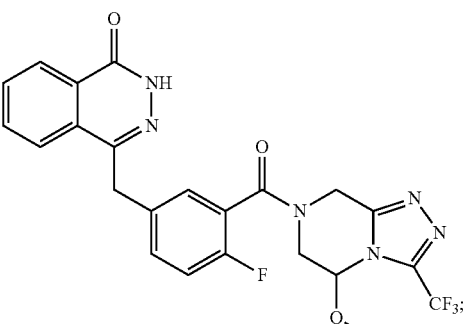

(S11)
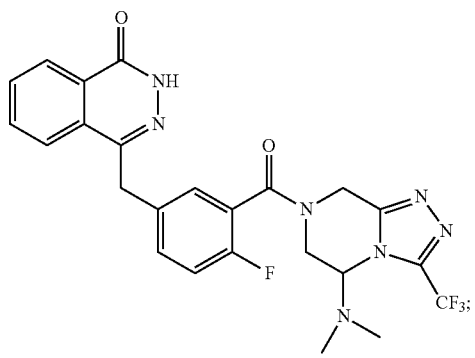
(S12)
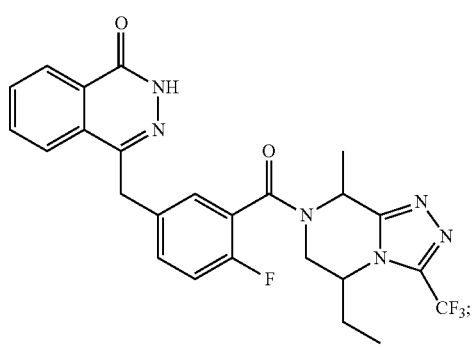
(S13)
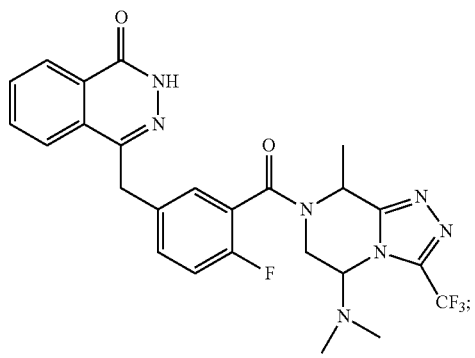
(S14)
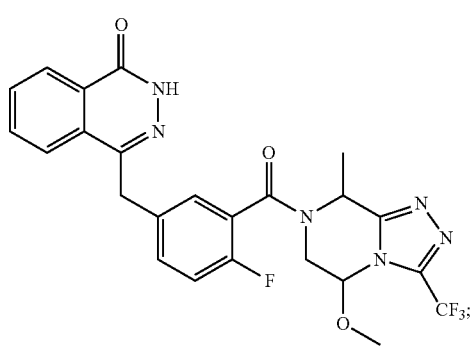
(S15)
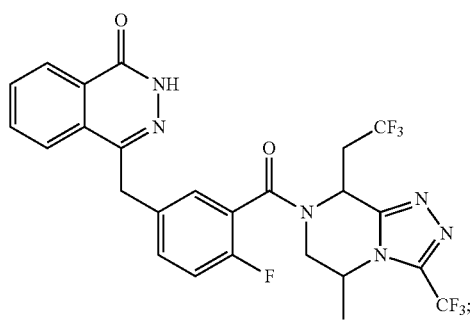
(S16)
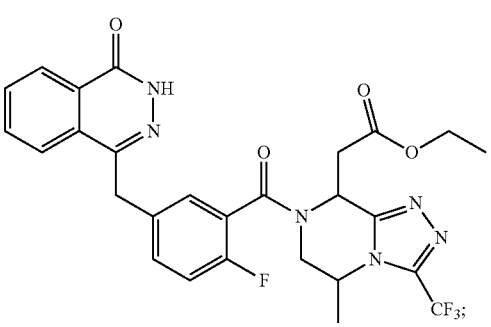
(S17)
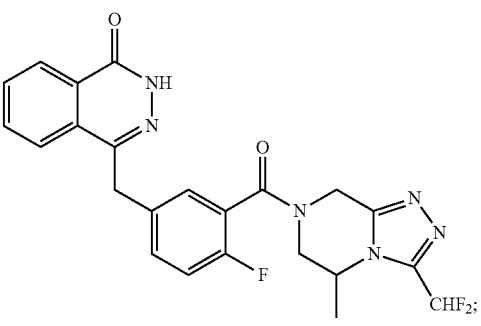
(S18)
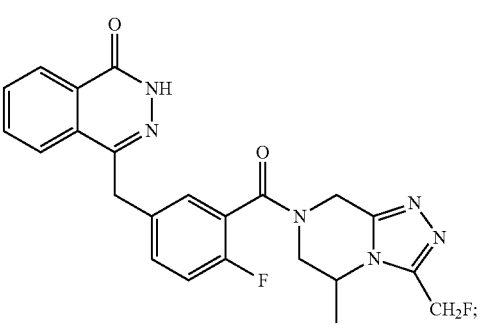
(S19)
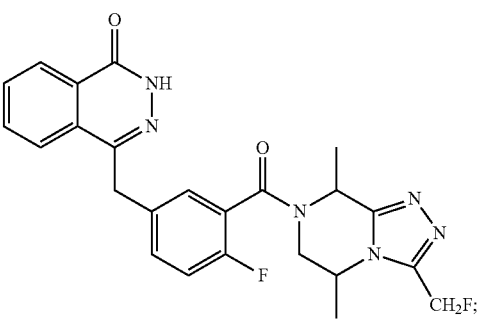

-continued (S20) 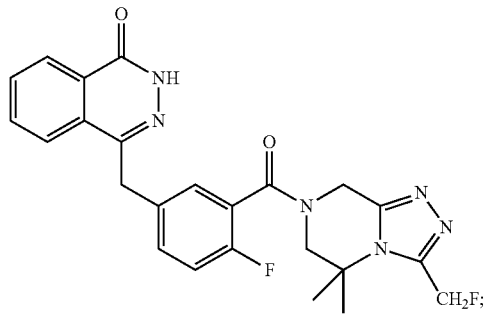

(S21) 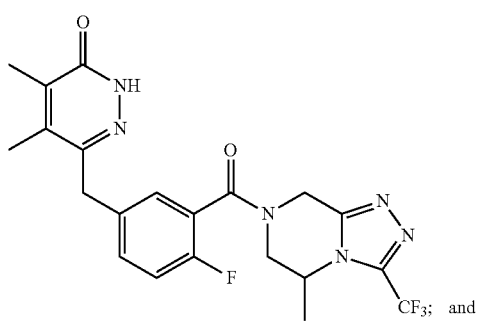

(S22) 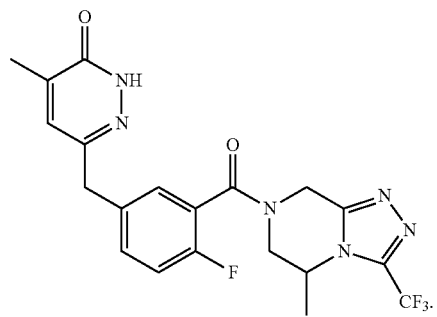

11. A pharmaceutical composition, comprising a pharmaceutically effective amount of a compound of claim 1, or a pharmaceutically acceptable salt or ester thereof, and a pharmaceutically acceptable carrier or excipient.

12. A method for modulating poly(adenosine diphosphate-ribose)polymerase-1 activity in a subject, the method comprising: administering to said subject the compound of claim 1.

13. The method of claim 12, wherein the subject suffers from a disease selected from the group consisting of an ischemic disease, a neurodegenerative disease and a cancer.

14. A method for preparing the compound of claim 1, comprising:

reacting a compound of formula D:

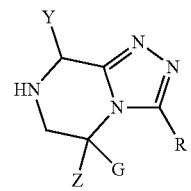

with a compound of formula S:

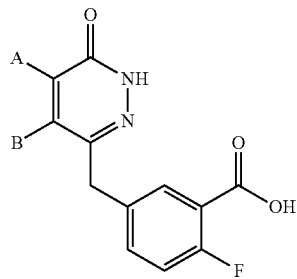

in the presence of 3-[bis(dimethylamino)methyliumyl]-3H-benzotriazol-1-oxide hexafluorophosphate, N,N-diisopropylethylamine and N,N-dimethylformamide.

* * * * *